(12) United States Patent
Gross et al.

(10) Patent No.: US 8,855,770 B2
(45) Date of Patent: Oct. 7, 2014

(54) DUODENAL EATING SENSOR

(75) Inventors: Yossi Gross, Moshav Mazor (IL); Yossi Roffeh, Netanya (IL); Radwin Khawaled, Shfar-am (IL); Jacob Benarie, Haifa (IL)

(73) Assignee: Betastim, Ltd., Caesarea (IL)

( * ) Notice: Subject to any disclaimer, the term of this patent is extended or adjusted under 35 U.S.C. 154(b) by 899 days.

(21) Appl. No.: 12/670,496

(22) PCT Filed: Jul. 24, 2008

(86) PCT No.: PCT/IL2008/001022
§ 371 (c)(1),
(2), (4) Date: Jul. 20, 2010

(87) PCT Pub. No.: WO2009/013749
PCT Pub. Date: Jan. 29, 2009

(65) Prior Publication Data
US 2010/0298741 A1    Nov. 25, 2010

Related U.S. Application Data

(60) Provisional application No. 60/961,916, filed on Jul. 24, 2007.

(51) Int. Cl.
*A61N 1/00* (2006.01)
*A61N 1/36* (2006.01)
(52) U.S. Cl.
CPC .................................. *A61N 1/36007* (2013.01)
USPC ............................................ 607/40; 600/593
(58) Field of Classification Search
CPC .... A61N 1/36007; A61N 1/05; A61N 1/0509
USPC ................ 60/593, 595; 600/593, 595; 607/40
See application file for complete search history.

(56) References Cited

U.S. PATENT DOCUMENTS

| | | |
|---|---|---|
| 3,411,507 A | 11/1968 | Wingrove |
| 5,540,730 A | 7/1996 | Terry, Jr. |
| 5,690,691 A | 11/1997 | Chen et al. |
| 5,813,993 A | 9/1998 | Kaplan |
| 5,836,994 A | 11/1998 | Bourgeois |
| 5,861,014 A | 1/1999 | Familoni |
| 5,995,872 A | 11/1999 | Bourgeois |

(Continued)

FOREIGN PATENT DOCUMENTS

| | | |
|---|---|---|
| EP | 0129483 | 12/1984 |
| WO | 2004043280 | 5/2004 |

(Continued)

OTHER PUBLICATIONS

Allen et al., "Relationships between electrical activities of antrum and duodenum", Section of Physiology, Mayo Clinic and Mayo Foundation, pp. 906-910, 1964.

(Continued)

*Primary Examiner* — Max Hindenburg
*Assistant Examiner* — Renee Danega
(74) *Attorney, Agent, or Firm* — RatnerPrestia

(57) ABSTRACT

Apparatus is described including a sensing electrode that detects electrical activity of a duodenum of a subject. The apparatus includes a control unit configured to facilitate a treatment of the subject responsively to the detected electrical activity. Other embodiments are also described.

26 Claims, 21 Drawing Sheets

(56) References Cited

U.S. PATENT DOCUMENTS

| | | |
|---|---|---|
| 6,104,955 A | 8/2000 | Bourgeois |
| 6,115,635 A | 9/2000 | Bourgeois |
| 6,535,764 B2 | 3/2003 | Imran |
| 6,571,127 B1 | 5/2003 | Ben-Haim |
| 6,579,301 B1 | 6/2003 | Bales |
| 6,591,137 B1 | 7/2003 | Fischell |
| 6,668,197 B1 | 12/2003 | Habib et al. |
| 6,826,428 B1 | 11/2004 | Chen et al. |
| 6,853,862 B1 | 2/2005 | Marchal |
| 6,994,095 B2 | 2/2006 | Burnett |
| 7,004,965 B2 | 2/2006 | Gross |
| 7,043,295 B2 | 5/2006 | Starkebaum |
| 7,054,690 B2 | 5/2006 | Imran |
| 7,076,305 B2 | 7/2006 | Imran |
| 7,076,306 B2 | 7/2006 | Marchal |
| 7,167,750 B2 | 1/2007 | Knudson et al. |
| 7,326,207 B2 | 2/2008 | Edwards |
| 7,430,450 B2 | 9/2008 | Imran |
| 7,676,270 B2 | 3/2010 | Imran |
| 7,742,818 B2 | 6/2010 | Dinsmoor et al. |
| 7,881,784 B2 | 2/2011 | Pasricha et al. |
| 7,881,797 B2 | 2/2011 | Griffin et al. |
| 7,967,750 B2 | 6/2011 | Chen et al. |
| 2001/0011543 A1 | 8/2001 | Forsell |
| 2003/0066536 A1 | 4/2003 | Forsell |
| 2003/0144708 A1 | 7/2003 | Starkebaum |
| 2003/0171685 A1* | 9/2003 | Lesser et al. ............... 600/509 |
| 2003/0181958 A1 | 9/2003 | Dobak |
| 2003/0208212 A1 | 11/2003 | Cigaina |
| 2004/0044376 A1 | 3/2004 | Flesler |
| 2004/0059393 A1 | 3/2004 | Policker |
| 2004/0088022 A1 | 5/2004 | Chen |
| 2004/0107004 A1 | 6/2004 | Levine |
| 2004/0167583 A1 | 8/2004 | Knudson |
| 2004/0172088 A1 | 9/2004 | Knudson |
| 2004/0176685 A1 | 9/2004 | Takizawa |
| 2005/0021101 A1 | 1/2005 | Chen et al. |
| 2005/0033331 A1 | 2/2005 | Burnett et al. |
| 2005/0055039 A1 | 3/2005 | Burnett et al. |
| 2005/0090873 A1 | 4/2005 | Imran |
| 2005/0222637 A1 | 10/2005 | Chen |
| 2005/0222638 A1 | 10/2005 | Foley |
| 2006/0142803 A1 | 6/2006 | Mintchev |
| 2006/0167497 A1 | 7/2006 | Armstrong et al. |
| 2006/0173238 A1 | 8/2006 | Starkebaum |
| 2006/0247717 A1* | 11/2006 | Starkebaum ............... 607/40 |
| 2007/0060971 A1 | 3/2007 | Glasberg et al. |
| 2007/0135856 A1 | 6/2007 | Knudson et al. |
| 2007/0150021 A1 | 6/2007 | Chen et al. |
| 2007/0162084 A1 | 7/2007 | Chen et al. |
| 2007/0250132 A1 | 10/2007 | Burnett |
| 2007/0293885 A1 | 12/2007 | Binmoeller |
| 2008/0177157 A1 | 7/2008 | Pasricha et al. |
| 2008/0183238 A1 | 7/2008 | Chen |
| 2009/0012154 A1 | 1/2009 | Pasricha et al. |
| 2009/0187206 A1 | 7/2009 | Binmoeller et al. |
| 2010/0191302 A1 | 7/2010 | Chen et al. |
| 2010/0228313 A1 | 9/2010 | Starkebaum et al. |
| 2011/0015695 A1 | 1/2011 | Pasricha et al. |
| 2011/0034967 A1 | 2/2011 | Chen et al. |
| 2011/0066208 A1 | 3/2011 | Pasricha et al. |
| 2011/0118747 A1 | 5/2011 | Pasricha et al. |
| 2011/0118812 A1 | 5/2011 | Pasricha et al. |

FOREIGN PATENT DOCUMENTS

| | | |
|---|---|---|
| WO | 2004078252 | 9/2004 |
| WO | 2004112563 | 12/2004 |
| WO | WO 2005/009288 A2 | 2/2005 |
| WO | 2005041749 | 5/2005 |
| WO | 2006035446 | 4/2006 |
| WO | WO 2006/047708 A2 | 5/2006 |
| WO | 2006102626 | 9/2006 |
| WO | 2006118790 | 11/2006 |

OTHER PUBLICATIONS

Schwartz et al., "Small Bowel Motility Affects Glucose Absorption in a Healthy Man", Diabetes Care, vol. 25, No. 10, Oct. 2002.

Y. Ruckebusch, "The Electrical Activity of the Digestive Tract of the Sheep As an Indication of the Mechanical Events in Various Regions", J. Physiol (1970), 210, pp. 857-882.

L. Bueno et al., "Rate of Flow of Digesta and Electrical Activity of the Small Intestine in Dogs and Sheep", J. Physiol. (1975), 249, pp. 69-85.

Michel Suter et al., "Laparoscopic Gastiric Banding A Prospective, Randomized Study Comparing the Lapband and the SAGB: Early Results", Annals of Surgery, vol. 241, No. 1, Jan. 2005, pp. 55-62.

Shemerovskii KA., "Effect of feeding on the activity of duodenal smooth muscle in dogs", Biull Eksp. Bio. Med. Oct. 1978; 86(10):394-7. (Abstract Only).

Yamada et al., (Effects of drugs on electromechanical activities of the stomach and duodenum of conscious dogs, Nippon Heikatsukin Gakkai Zasshi, Feb. 1983; 19(1):25-35. (Abstract Only).

Andersson et al., "Gastric electrical stimulation for intractable vomiting in patients with chronic intestinal pseudoobstruction," Neurogastroenterol Motil (2006) 18, 823-830.

Busch et al., "Electrical Stimulation of the Duodenum to Treat Diabetes Mellitus Type 2 in Obese Patients—Preliminary Results of the First in Men Study," SSAT 51$^{st}$ Annual Meeting 2010 Program and Abstracts Overview.

Byun et al., "Radiofrequency Ablation of the Gastrointestinal Tract with a Stent-Like Electrode: Experimental Study," Korean 3 Radiol 4(1), Mar. 2003, 19-26.

Chen et al., "Electrical Pacing Accelerates Intestinal Transit Slowed by Fat-Induced Ileal Brake," Digestive Diseases and Sciences, vol. 48, No. 2 (Feb. 2003), 251-256.

Grundfest-Broniatowski et al., "Voluntary Control of an Ileal Pouch by Coordinated Electrical Stimulation A Pilot Study in the Dog," Dis. Col. & Rect. Apr. 1988, 261-267.

Khawaled et al., "Intestinal electrical stimulation decreases postprandial blood glucose levels in rats," Surgery for Obesity and Related Diseases 5 (2009) 692-697.

Liu et al., "Therapeutic Potential of Duodenal Electrical Stimulation for Obesity: Acute Effects on Gastric Emptying and Water Intake," American Journal of Gastroenterology 2005;100:792-796.

McCloy et al., "Duodenal pH in health and duodenal ulcer disease: effect of a meal, Coca-Cola, smoking, and cimetidine," Gut, 1984, 25, 386-392.

Nguyen et al., "Abnormal postprandial duodenal chime transport in patients with long standing insulin dependent diabetes mellitus," Gut 1997; 41: 624-631.

Sun et al., "Intestinal Electric Stimulation Decreases Fat Absorption in Rats: Therapeutic Potential for Obesity," Obes. Res. Aug. 2004; 12(8): 1235-1242.

Xu et al., "Effects and Mechanisms of Electrical Stimulation of the Stomach, Duodenum, Ileum, and Colon on Gastric Tone in Dogs," Dig Dis Sci (2010) 55:895-901.

Xu et al., "Gastric/Intestinal Electrical Stimulation Modulates Appetite Regulatory Peptide Hormones in the Stomach and Duodenum in Rats," Obesity Surgery, 17, 2007, 406-413.

Yin et al., "Potential of Intestinal Electrical Stimulation for Obesity: A Preliminary Canine Study," Obesity vol. 15 No. 5 May 2007, 1133-1138.

Zhao et al., "Inhibitory effects and mechanisms of intestinal electrical stimulation on gastric tone, antral contractions, pyloric tone, and gastric emptying in dogs," Am J Physiol Regul Integr Comp Physiol 296: R36-R42, 2009.

* cited by examiner

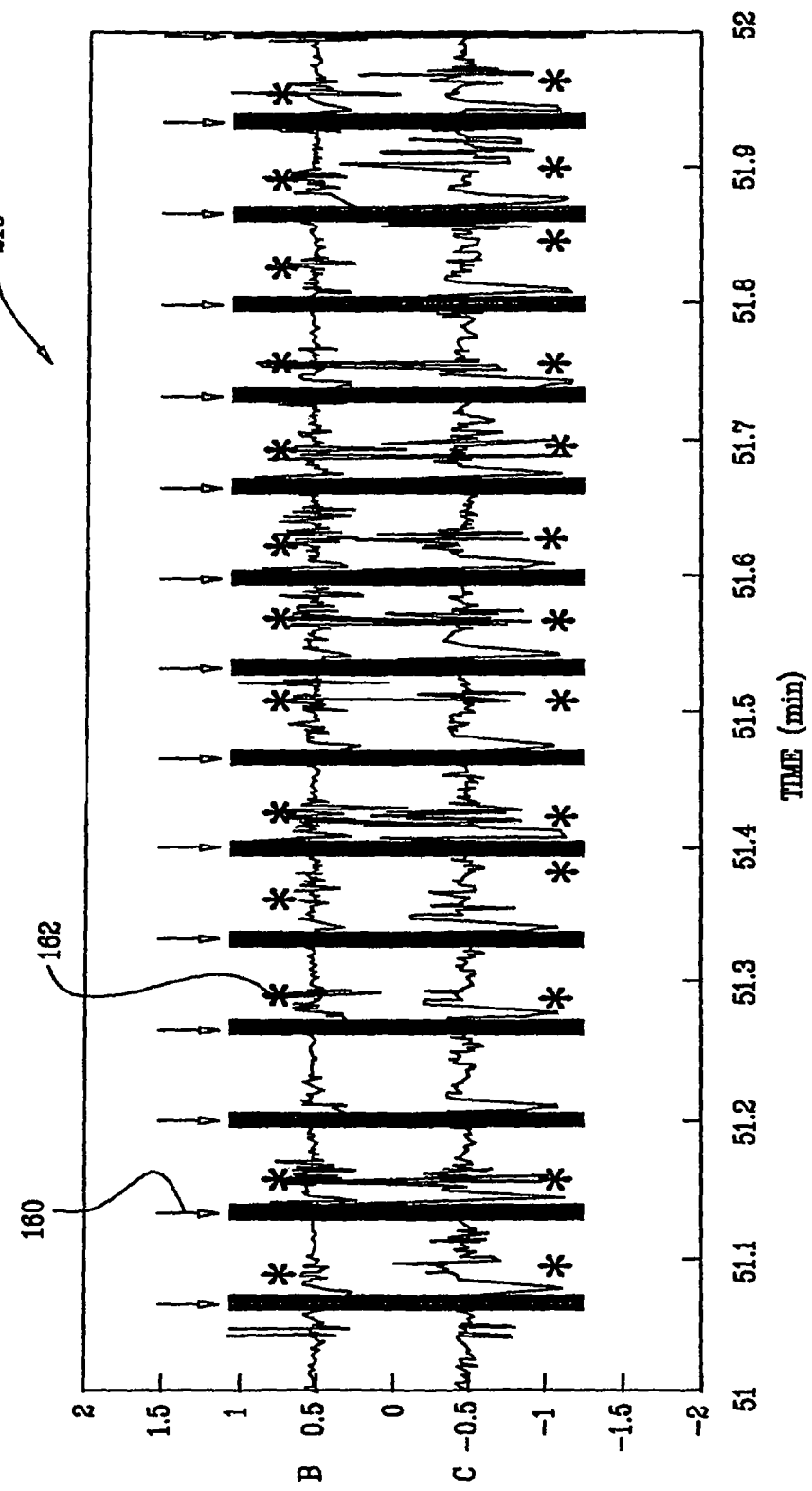

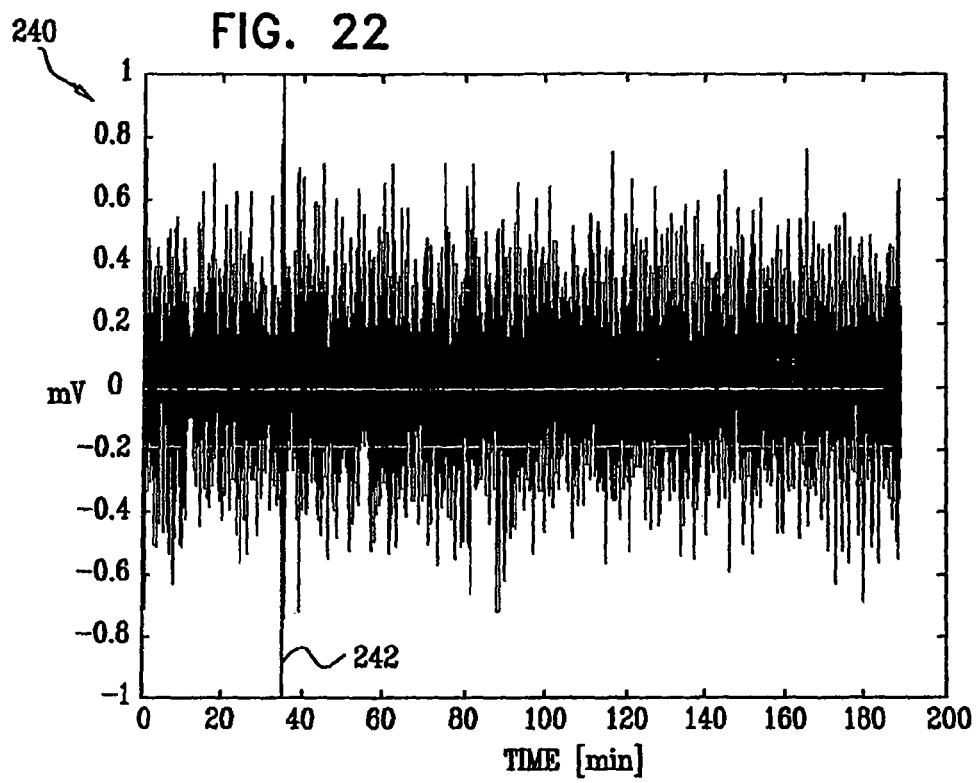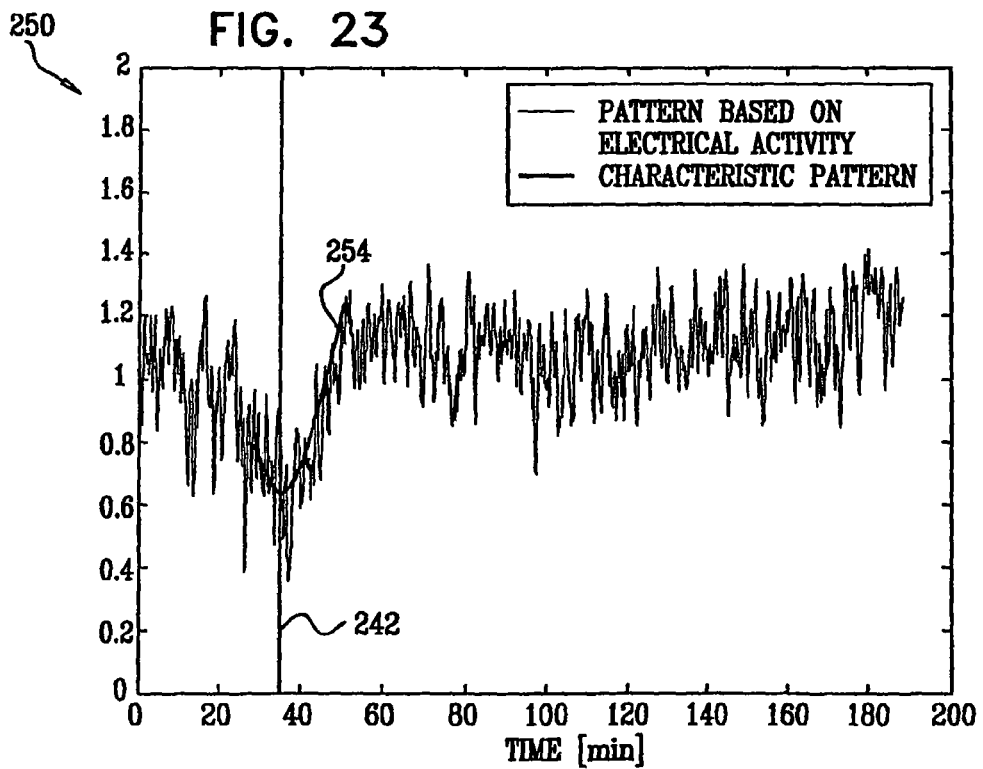

DUODENAL EATING SENSOR

CROSS-REFERENCES TO RELATED APPLICATIONS

The present patent application is a U.S. National Phase Application of PCT Application No. PCT/IL2008/001022 to Gross et al., filed Jul. 24, 2008, which claims the benefit of U.S. Provisional Patent Application 60/961,916 to Gross et al., entitled "Duodenal eating sensor," filed Jul. 24, 2007, which is incorporated herein by reference.

FIELD OF THE INVENTION

The present invention generally relates to implanted medical apparatus. Specifically, the present invention relates to eating detection.

BACKGROUND OF THE INVENTION

Bariatrics, a branch of medicine which deals with the treatment of obesity, has become increasingly important as the prevalence of obesity has been increasing for two decades and continues to rise.

PCT Publication WO 06/035446 to Karasik, which is incorporated herein by reference, describes an apparatus and a method for treating a weight disorder in a subject. The apparatus comprises an implantable device such as an inflatable balloon and electrodes capable of sensing a physiological change associated with food ingestion or hunger and a mechanism adapted for directly stimulating a region such as the duodenum which is responsive to a gastrointestinal satiety agent. Such a mechanism can be a drug reservoir containing a drug such as CCK or analogs thereof which is contained within an inflatable balloon being implantable in a stomach of the subject. The apparatus and method provided are described as combining synergistic approaches to limiting meal size, i.e., chemo and mechano receptor activation of vagal satiety stimuli, electric stimulation of specific vagal pathways and limitations of gastric space.

U.S. Pat. No. 6,115,635 to Bourgeois, which is incorporated herein by reference, describes a method and apparatus for providing electrical stimulation of the gastrointestinal tract. The apparatus features an implantable pulse generator which may be coupled to the gastric system through one or more medical electrical leads. In the preferred embodiment the leads couple to the circular layer of the stomach. The pulse generator preferably features sensors for sensing gastric electrical activity, and in particular, whether peristaltic contractions are occurring. One embodiment is described as particularly solving the problem of accurately detecting gastric arrhythmias by periodically reverting into a sensed intrinsic gastric rhythm mode. In this mode the output of electrical stimulation is adjusted to only occur at an exceedingly slow rate. This slow rate of stimulation thus permits the gastrointestinal tissues to undergo an intrinsic depolarization so that the underlying intrinsic slow wave rate may be detected.

U.S. Pat. No. 7,043,295 to Starkebaum, which is incorporated herein by reference, describes methods and systems for treating patients suffering from eating disorders, e.g. obesity, through the dispensation of a drug by an implantable infusion pump delivering drug into the cerebral spinal fluid (CSF) at a site of the intrathecal space in amounts and at times effective to suppress the patient's appetite through interaction of the drug transported through the CSF with receptors in the brain. Delivery of a programmed drug dosage is preferably at a programmed time (or at programmed times) of day, in response to a command received from the patient, or in response to a trigger signal developed from a sensed GI tract signal accompanying peristalsis.

US Patent Application Publication 2003/0144708 to Starkebaum, which is incorporated herein by reference, describes methods and systems for treating patients suffering from eating disorders, e.g. obesity, through the delivery of electrical stimulation directly or indirectly to the pylorus of a patient in an effective stimulation regimen to substantially close the pylorus lumen to inhibit emptying of the stomach. The stimulation electrodes are applied directly to or immediately adjacent to the muscle layers of the pyloric sphincter, or are situated in operative relation to the splanchnic nerve that innervates the pyloric sphincter. Stimulation can be delivered continuously 24 hours per day, or can be halted at meal times to enable passage of chyme through the pylorus lumen at such times. Alternatively, stimulation is described as being delivered following events related to peristalsis, ingestion or stomach emptying, to induce a feeling of satiety.

An article entitled "Effect of feeding on the activity of duodenal smooth muscle in dogs," by Shemerovskii, Biull Eksp Biol Med. 1978 October; 86(10):394-7, which is incorporated herein by reference, describes an investigation into the electric activity of the duodenum smooth muscles with chronically implanted electrodes. This activity after feeding was compared with that in fasting during the time equal to the period of rest and the active period of the duodenum in fasting. The number of pacesetter potentials was identical during digestion and fasting. The number of spike potentials was significantly different during these compared states. The relationship of the "digestive" and "hungry" electrical activities of the duodenum depended both on the compared type of potential and on the compared time periods.

PCT Application WO 06/102626 to Policker et al., which is incorporated herein by reference, describes apparatus including a control unit, adapted to be implanted within a patient, and a corkscrew-shaped electrode mount, adapted to be implanted in a wall of a stomach of the patient. The corkscrew-shaped electrode mount includes first and second electrodes, at respective sites of the electrode mount, and a controller, wirelessly coupled to the control unit. Other embodiments are also described.

An article entitled "Small Bowel Motility Affects Glucose Absorption in a Healthy Man" by Schwartz, Diabetes Care, Volume 25, Number 10, October 2002, which is incorporated herein by reference, describes an investigation into the relationship between duodenojejunal motor activity and glucose absorption and an evaluation of the effect of modification of duodenojejunal motility on glucose absorption by using the prokinetic drug cisapride. The main findings of the study are described as being that, in healthy subjects, an increase in number of duodenojejunal pressure waves and antegrade propagated pressure waves was related to an increase in small intestinal glucose absorption; treatment with cisapride increased the mean amplitude of duodenojejunal pressure waves, but did not affect the number of pressure waves and spatiotemporal organization of antegrade propagated pressure waves and cisapride treatment did not affect glucose absorption.

An article entitled "The electrical activity of the digestive tract of the sheep as an indication of the mechanical events in various regions," by Rukebusch, J. Physiol. (1970), 210, pp. 857-882, which is incorporated herein by reference, describes a method used in conscious sheep for recording oscillographically the electrical potentials led from enamelled stainless-steel wires implanted in the wall of the stomach and intestine. Slow waves characterized by cyclically recurring and rhythmic fluctuations in voltage were described as having been recorded, together with the superimposed fast activity or burst of spikes when the muscle is contracting. The whole activity is described as comprising a distinguishable pattern of grouped discharge which is synchronous with mechanical events within different regions of the alimentary tract. The relationship between electrical and mechanical activity of the reticulo-rumenal movements was examined at rest, and during feeding and ruminating. Electrical correlates of motor activity in the small bowel were investigated under different dietary regimens.

An article entitled "Rate of flow of digesta and electrical activity of the small intestine in dogs and sheep," by Bueno, J Physiol. (1975), 249, pp. 69-85, which is incorporated herein by reference, describes experiments that were undertaken on dogs and sheep (i) to investigate the relation between the migrating myoelectric complex and the rate of passage of digesta along the small intestine; (ii) to analyze the influence of the irregular spiking phase and of the regular spiking phase on the mean velocity of the intestinal contents; (iii) to emphasize the function of the migrating myoelectric complex as a permanent moving process which regulates the flow of intestinal contents. It concludes that in the fasted dog and in the sheep, the migrating myoelectric complex controls the pressure gradients on which the flow of intestinal contents depends. This is accomplished in the main by the prolonged phase of irregular spiking activity, and it is suggested that the regular spiking activity which follows it, though not in itself propulsive, serves as a barrier to prevent backflow of digesta into the quiescent part of the intestine. When continuous spiking activity is induced, by feeding in the dog and by injection of 5-hydroxytryptophan in the sheep, no part of the intestine is quiescent and the transit time is shortened by the incessant irregular spiking activity.

An article entitled "Relationships between electrical activities of antrum and duodenum," by Allen, Am. J. Physiol. 207(4): 906-910, 1964, which is incorporated herein by reference, describes a study that attempted to determine whether the slow basic electrical rhythms of the antrum and the duodenum were related, and to search for relationships between the fast electrical activities of the two regions. Observations were made on five healthy, trained, unanaesthetized dogs by means of detecting electrodes surgically implanted on the walls of the antrum and duodenum. No relationship was found, in either fasted or fed dogs, between the slow electrical rhythms of the antrum and duodenum. Feeding increased the fast activity in the antrum and in the duodenum, and under these circumstances, the fast activity in the duodenum was related to the slow basic electrical rhythm of the antrum.

The following patents and patent applications, which are incorporated herein by reference, may be of interest:
U.S. Pat. No. 7,076,306 to Marchal et al.
U.S. Pat. No. 7,076,305 to Imran et al.
U.S. Pat. No. 7,054,690 to Imran
U.S. Pat. No. 7,004,965 to Gross
U.S. Pat. No. 6,853,862 to Marchal et al.
U.S. Pat. No. 6,591,137 to Fischell et al.
U.S. Pat. No. 6,579,301 to Bales et al.
U.S. Pat. No. 6,571,127 to Ben-Haim et al.
U.S. Pat. No. 6,535,764 to Imran et al.
U.S. Pat. No. 6,104,955 to Bourgeois
U.S. Pat. No. 5,995,872 to Bourgeois
U.S. Pat. No. 5,861,014 to Familoni
U.S. Pat. No. 5,836,994 to Bourgeois
U.S. Pat. No. 5,813,993 to Kaplan et al.
U.S. Pat. No. 5,540,730 to Terry et al.
European Patent 0,129,483 to Shturman et al.
US Patent Application Publication 2006/0173238 to Starkebaum
US Patent Application Publication 2006/0142803 to Mintchev
US Patent Application Publication 2005/0222638 to Foley et al.
US Patent Application Publication 2005/0090873 to Imran
US Patent Application Publication 2004/0176685 to Takizawa et al.
US Patent Application Publication 2004/0172088 to Knudson et al.
US Patent Application Publication 2004/0167583 to Knudson et al.
US Patent Application Publication 2004/0107004 to Levine et al.
US Patent Application Publication 2004/0059393 to Policker et al.
US Patent Application Publication 2004/0044376 to Flesler et al.
US Patent Application Publication 2003/0208212 to Cigaina
US Patent Application Publication 2003/0181958 to Dobak III
US Patent Application Publication 2003/0066536 to Forsell
US Patent Application Publication 2001/0011543 to Forsell
PCT Application WO 06/118790 to Maschino et al.
PCT Application WO 05/041749 to Imran
PCT Application WO 04/112563 to Ben-Haim et al.
PCT Publication WO 04/078252 to Karashurov
PCT Publication WO 04/043280 to Utley et al.

The following articles, which are incorporated herein by reference, may be of interest:

Jean-Marie Calmes et al., "Laparoscopic Gastric Banding: A Prospective, Randomized Study Comparing the Lapband and the SAGB: Early Results CME," Annals of Surgery (Mar. 2, 2005)

Yamada et al., "Effects of drugs on electromechanical activities of the stomach and duodenum of conscious dogs," Nippon Heikatsukin Gakkai Zasshi. 1983 February; 19(1): 25-35

SUMMARY OF THE INVENTION

In some embodiments of the present invention, a duodenal sensor detects electrical activity in the duodenum of a subject in order to determine whether the subject is eating. A treatment is initiated upon detection that the subject is eating.

Typically, the treatment includes the inducement of a feeling of satiety in an obese subject, which causes the subject to ingest less than the subject would otherwise have ingested. Alternatively or additionally, the GI tract of an obese subject is treated to decrease the digestion and/or the absorption of food which the subject ingests. In alternative embodiments, a treatment is initiated which increases the digestion and/or the absorption of food in the GI tract of a malnourished subject.

In some embodiments of the invention, the treatment comprises inducing a feeling of satiety in the subject. For some applications, the volume of the subject's stomach is reduced by inflating a balloon inside the stomach. Alternatively or additionally, a band placed around the stomach of the subject is tightened.

In some embodiments, ingested food is retained in the stomach by closing the pylorus of the subject. Alternatively or additionally, an electrical current is driven toward the stomach to reduce the gastric motility of the subject, and/or to modulate gastric wall tension.

For some applications, the absorption of food through the duodenum is regulated by driving a current toward the duodenum to regulate intestinal motility, and/or intestinal permeability. Alternatively or additionally, the permeability of a sheath placed in the duodenum is regulated.

For some applications, an additional sensor detects if the subject is unlikely to be eating, and initiation of the treatment is withheld in response to such a detection. Alternatively or additionally, the apparatus is configured to withhold the detection of duodenal electrical activity when the additional sensor indicates that the subject is unlikely be eating.

In some embodiments, the additional sensor comprises a respiration sensor configured to provide an indication that the subject is sleeping and is unlikely to be eating. Alternatively or additionally, the additional sensor comprises an angle sensor configured to detect the angle at which the subject's body is disposed. If the subject is horizontal, for example, it is an indication that the subject is sleeping, or otherwise in a position in which the subject is unlikely to be eating.

Further alternatively or additionally, the apparatus includes a cardiac sensor configured to detect cardiac events of the subject and to withhold treatment, or duodenal sensing, responsively. For example, the apparatus may be configured to withhold the treatment if the heart rate of the subject is not between an upper and a lower threshold. If the heart rate of the subject exceeds the upper threshold, this indicates that the subject is exercising, and if it is below the lower threshold it indicates that the subject is sleeping. Still further alternatively or additionally, the apparatus comprises an acceleration sensor, and the apparatus is configured to withhold the treatment when recent measurements indicate that the subject is exercising or engaged in similar activity, or is sleeping.

For some applications, the duodenal sensor comprises a duodenal electrode which is helical. In order to implant the electrode, an incision is made in the wall of the duodenum. The electrode is advanced through the inside of the duodenum and then rotated through the incision a plurality of times, so that it becomes coupled to the outside of the duodenum. Alternatively or additionally, the electrode is disposed on the inside of a ring, or the electrode itself is ring shaped. The ring, or the ring electrode, is implanted laparoscopically and is placed around the outside of the duodenum.

In some embodiments of the invention, one or more capsules, which are configured to emit a signal when situated in the duodenum, are administered to a subject. Typically, the capsules comprise one or more electrodes coated with a duodenum-sensitive coating. Upon reaching the duodenum, the coating dissolves, facilitating the emission of the signal. The signals of the one or more capsules are processed to determine characteristics of the subject's GI tract, for example, the gastric emptying half-time.

There is therefore provided, in accordance with an embodiment of the present invention, apparatus, including:

a sensing electrode configured to detect electrical activity of a duodenum of a subject; and a control unit configured to facilitate a treatment of the subject responsively to the detected electrical activity.

In an embodiment, the sensing electrode is configured to detect slow wave energy of the duodenum, and the control unit is configured to initiate the treatment responsively to the detected slow wave energy.

In an embodiment, the sensing electrode is configured to detect a frequency component of slow waves of the duodenum, and the control unit is configured to initiate the treatment responsively to the detected slow wave frequency component.

In an embodiment, the sensing electrode is configured to detect a rate of slow wave activations of the duodenum, and the control unit is configured to initiate the treatment responsively to the detected rate of slow wave activations.

In an embodiment, the control unit is configured to be implanted in the subject.

In an embodiment, the control unit is configured to withhold facilitating the treatment in response to a detection that the subject is asleep.

In an embodiment, the control unit includes a sensor configured to detect acceleration of the subject and to modulate the treatment in response thereto.

In an embodiment, the control unit includes a respiration sensor configured to detect respiration of the subject and to modulate the treatment in response thereto.

In an embodiment, the apparatus further includes a balloon configured to be disposed within a stomach of the subject, and the control unit is configured to facilitate the treatment by inflating the balloon.

In an embodiment, the control unit is configured to facilitate the treatment by facilitating a mechanical closure of a pylorus of the subject.

In an embodiment, the apparatus further includes a band configured to be implanted around a stomach of the subject, and the control unit is configured to facilitate the treatment by tightening the band.

In an embodiment, the control unit is configured to facilitate the treatment by closing a pylorus of the subject by driving a current into gastrointestinal tract tissue of the subject.

In an embodiment, the control unit includes a sensor configured to detect an angle at which the body of the subject is disposed and to modulate the treatment in response thereto.

In an embodiment, the control unit is configured to withhold facilitating the treatment in response to a detection that the subject is horizontal.

In an embodiment, the control unit is configured to detect a cardiac event of the subject and to modulate the treatment in response thereto.

In an embodiment, the control unit is configured to detect a heart rate of the subject and to withhold facilitating the treatment when the detected heart rate indicates that the subject is exercising.

In an embodiment, the control unit is configured to detect a heart rate of the subject and to withhold facilitating the treatment when the detected heart rate indicates that the subject is sleeping.

In an embodiment, the apparatus further includes a treatment electrode configured to be coupled to a stomach of the subject, and the control unit is configured to facilitate the treatment by driving electrical current into the stomach, via the treatment electrode.

In an embodiment, the control unit is configured to modulate tension of a gastric wall of the subject by driving the current into the stomach.

In an embodiment, the control unit is configured to increase gastric motility of the subject, by driving the current into the stomach.

In an embodiment, the control unit is configured to reduce gastric motility of the subject by driving the current into the stomach.

In an embodiment, the control unit is configured to facilitate the treatment by driving electrical current into the duodenum.

In an embodiment, the control unit is configured to increase intestinal permeability of the subject by driving the current.

In an embodiment, the control unit is configured to decrease intestinal permeability of the subject by driving the current.

In an embodiment, the control unit is configured to increase intestinal motility of the subject by driving the current.

In an embodiment, the control unit is configured to decrease intestinal motility of the subject by driving the current.

In an embodiment, the apparatus further includes a sheath configured to be disposed within the duodenum.

In an embodiment, the apparatus further includes a treatment electrode coupled to the sheath.

In an embodiment, the control unit is configured to facilitate the treatment by regulating permeability of the sheath.

In an embodiment, the apparatus further includes a ring coupled to the sensing electrode, configured to couple the sensing electrode to the duodenum by being implanted around an outside of the duodenum.

In an embodiment, the ring is configured to be implanted laparoscopically.

In an embodiment, the ring is configured to be implanted endoscopically.

In an embodiment, the sensing electrode includes a ring electrode configured to be implanted around an outside of the duodenum.

In an embodiment, the ring electrode is configured to be implanted laparoscopically.

In an embodiment, the ring electrode is configured to be implanted endoscopically.

In an embodiment, the control unit is configured to calculate a pattern based on changes in the detected electrical activity over time, the control unit includes a pattern recognition unit configured to compare the calculated pattern to a characteristic pattern, and the control unit is configured to facilitate the treatment of the subject responsively to the comparing.

In an embodiment, the pattern recognition unit is configured to compare the calculated pattern to the characteristic pattern irrespective of a magnitude of the electrical activity detected by the sensing electrode.

In an embodiment, the pattern recognition unit is configured to compare the calculated pattern to the characteristic pattern irrespective of relative magnitudes of the calculated pattern and the characteristic pattern.

In an embodiment, the pattern recognition unit is configured to compare the calculated pattern to the characteristic pattern by comparing magnitudes of the calculated pattern and of the characteristic pattern.

In an embodiment, the characteristic pattern includes a v-shaped pattern, and the pattern recognition unit is configured to compare the calculated pattern to the v-shaped pattern.

In an embodiment, the control unit is configured to calculate the pattern based on changes in activation energy of the detected electrical activity over time.

In an embodiment, the control unit is configured to calculate the pattern based on changes in number of activations of the detected electrical activity per unit time.

In an embodiment, the control unit is configured to calculate the pattern based on changes over time of a parameter of the detected electrical activity selected from the group consisting of slow-wave energy, time frequency distribution, and number of activations of slow-waves per unit time.

In an embodiment, the characteristic pattern includes a pattern that lasts more than five minutes, and the pattern recognition unit is configured to compare the calculated pattern to the pattern that lasts more than five minutes.

In an embodiment, the characteristic pattern includes a pattern that lasts more than 15 minutes, and the pattern recognition unit is configured to compare the calculated pattern to the pattern that lasts more than 15 minutes.

In an embodiment, the control unit is configured to calculate the pattern based on changes in a plurality of parameters of the detected electrical activity over time.

In an embodiment, the parameters include an activation energy of the detected electrical activity and a number of activations of the detected electrical activity per unit time, and the control unit is configured to calculate the pattern based on changes in the activation energy and the number of activations of the detected electrical activity per unit time.

In an embodiment, the parameters include a plurality of parameters of the detected electrical activity selected from the group consisting of activation energy, number of activations per unit time, slow-wave energy, time frequency distribution, and number of activations of slow-waves per unit time, and the control unit is configured to calculate the pattern based on changes in the selected parameters over time.

In an embodiment, the characteristic pattern includes an eating pattern that is characteristic of a person who is eating, and the pattern recognition unit is configured to compare the calculated pattern to the eating pattern.

In an embodiment, the control unit includes a template assessment unit configured to determine a subject-eating pattern that is characteristic of the subject when the subject is eating, and the pattern recognition unit is configured to compare the calculated pattern to the subject-eating pattern.

In an embodiment, the template assessment unit is configured to determine the subject-eating pattern during a calibration period, and the pattern recognition unit is configured to compare the calculated pattern to the subject-eating pattern subsequent to the calibration period.

In an embodiment, subsequent to the pattern recognition unit comparing the calculated pattern to the subject-eating pattern, the template assessment unit is configured to determine if the subject-eating pattern has changed, and to update the subject-eating pattern in response to the subject-eating pattern having changed.

In an embodiment, the pattern recognition unit is configured to compare the calculated pattern to the characteristic pattern by comparing a calculated pattern based on at least 2 minutes of the detected electrical activity to the characteristic pattern.

In an embodiment, the pattern recognition unit is configured to compare the calculated pattern to the characteristic pattern by comparing a calculated pattern based on 15-30 minutes of the detected electrical activity to the characteristic pattern.

In an embodiment, the pattern recognition unit is configured to compare the calculated pattern to the characteristic pattern by generating a cross-correlation coefficient indicative of a level of correlation between the calculated pattern and the characteristic pattern.

In an embodiment, the control unit is configured to facilitate the treatment of the subject by:

analyzing the detected electrical activity to identify an indication that the subject may be eating, in an interim treatment mode, facilitating the treatment in response to the analysis of the detected electrical activity, and stopping the treatment in response to the cross-correlation coefficient not passing a threshold.

In an embodiment, the control unit is configured to facilitate the treatment of the subject responsively to the comparing by facilitating the treatment in response to the cross-correlation coefficient passing a threshold.

In an embodiment, the control unit is configured to facilitate administration of a pharmaceutical to the subject in response to the cross-correlation coefficient passing the threshold.

In an embodiment, the control unit is configured to drive current into tissue of the subject in response to the cross-correlation coefficient passing the threshold.

There is additionally provided, in accordance with an embodiment of the present invention, a method, including:
detecting electrical activity of a duodenum of a subject; and
treating the subject in response to the detected electrical activity.

There is further provided, in accordance with an embodiment of the present invention, apparatus, including:
a plurality of capsules, each of the capsules being configured to emit a characteristic detectable signal when situated in a duodenum of a subject;
a detector configured to detect the characteristic signals; and
a control unit coupled to the detector, and configured to determine a gastric emptying rate of the subject by processing the detected characteristic signals.

In an embodiment, each of the capsules includes a dissolvable coating configured to dissolve inside the duodenum.

In an embodiment, each of the capsules includes one or more electrodes configured to emit the detectable signal.

In an embodiment, the detector includes a patch configured to be placed on the outside of the subject.

There is additionally provided, in accordance with an embodiment of the present invention, a method, including:
administering a plurality of capsules to a subject, each of the capsules being configured to emit a characteristic detectable signal when situated in a duodenum of a subject; and
determining a gastric emptying rate of the subject by detecting and processing the characteristic signals.

There is further provided, in accordance with an embodiment of the present invention, apparatus, including:
a helical electrode;
an incision tool, configured to make an incision in a side of a lumen; and
an implanting device configured to couple the electrode to the outside of the lumen by advancing the electrode through the lumen and subsequently rotating the electrode a plurality of times through the incision in the lumen.

There is additionally provided, in accordance with an embodiment of the present invention, a method, including:
making an incision in a side of a lumen; and
coupling a helical electrode to the outside of the lumen by advancing the electrode through the lumen and subsequently rotating the electrode a plurality of times though the incision in the lumen.

There is further provided, in accordance with an embodiment of the present invention, a method, including:
detecting electrical activity;
calculating a pattern based on changes over time of a parameter of the detected electrical activity selected from the group consisting of: activation energy, number of activations per unit time, and time frequency distribution; and
generating a cross-correlation coefficient by comparing the calculated pattern to a characteristic pattern.

In an embodiment, calculating the pattern includes calculating a pattern based on changes over time of a plurality of the parameters of the detected electrical activity.

In an embodiment, comparing the calculated pattern to the characteristic pattern includes comparing the pattern to the characteristic pattern irrespective of a magnitude of the detected electrical activity.

In an embodiment, comparing the calculated pattern to the characteristic pattern includes comparing the pattern to the characteristic pattern irrespective of relative magnitudes of the calculated pattern and the characteristic pattern.

In an embodiment, comparing the calculated pattern to the characteristic pattern includes comparing magnitudes of the calculated pattern and of the characteristic pattern.

In an embodiment, comparing the calculated pattern to the characteristic pattern includes comparing the calculated pattern to a pattern that lasts more than five minutes.

In an embodiment, comparing the calculated pattern to the characteristic pattern includes comparing the calculated pattern to a pattern that lasts more than 15 minutes.

In an embodiment, comparing the calculated pattern to the characteristic pattern includes comparing a calculated pattern based on at least 2 minutes of the detected electrical activity to the characteristic pattern.

In an embodiment, comparing the calculated pattern to the characteristic pattern includes comparing a calculated pattern based on 15-30 minutes of the detected electrical activity to the characteristic pattern.

The present invention will be more fully understood from the following detailed description of embodiments thereof, taken together with the drawings, in which:

BRIEF DESCRIPTION OF THE DRAWINGS

FIG. 11 is a graph illustrating the effect of driving a current toward a pigs duodenum on the recorded duodenal electrical activity, measured in accordance with an embodiment of the present invention;

FIG. 22 is a graph of electrical activity recorded in a pig's duodenum, in accordance with an embodiment of the present invention;

FIG. 23 is a graph of the geometric mean of (a) the duodenal activation energy and (b) the number of activations per unit time, based on the electrical activity of FIG. 22, calculated in accordance with an embodiment of the present invention;

DETAILED DESCRIPTION OF EMBODIMENTS

Figure 1:
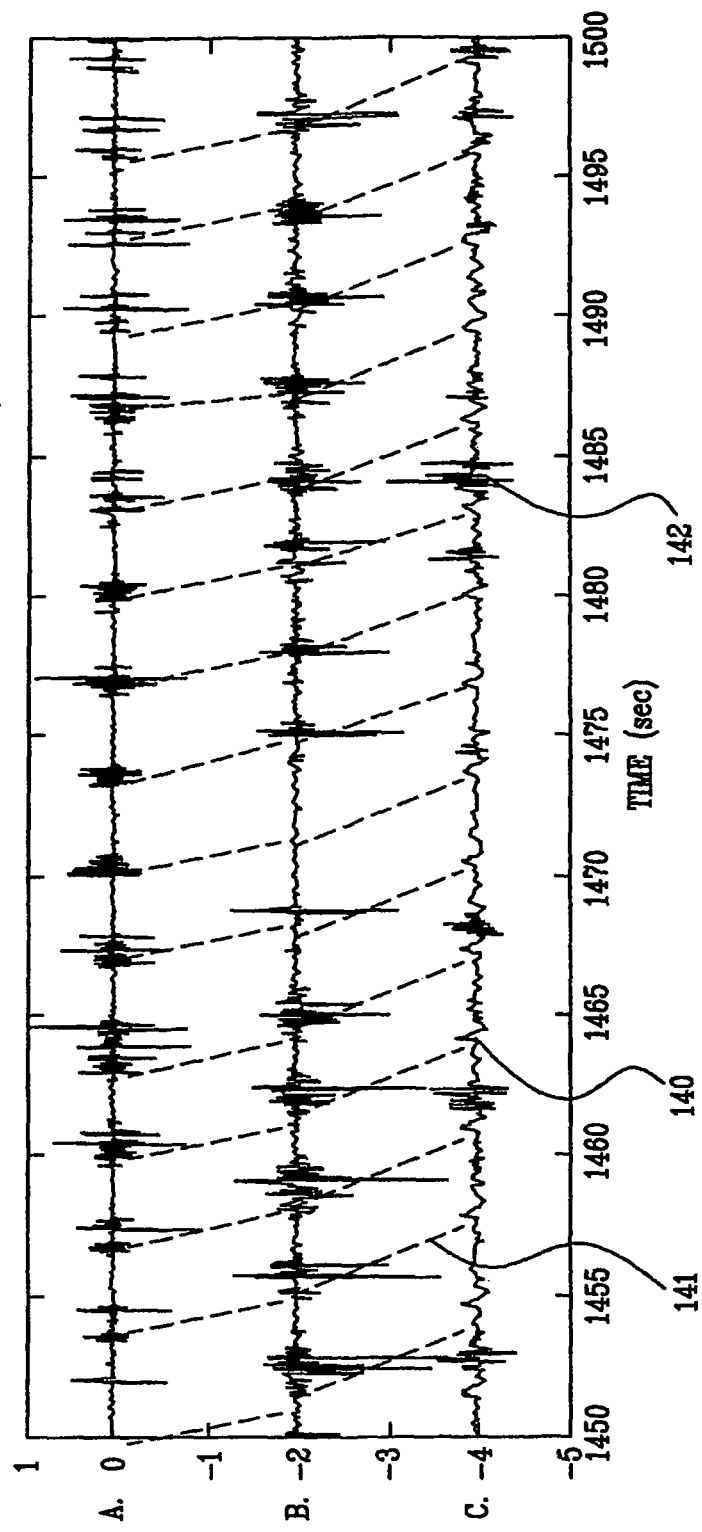
FIG. 1 is graph illustrating duodenal electrical activity recorded in a fasting pig, measured in accordance with an embodiment of the present invention.

Reference is now made to FIG. 1, which is a graph 220 illustrating duodenal electrical activity, recorded in a fasting pig, in accordance with an embodiment of the present invention. Curves A, B and C show, respectively, the electrical activity which was recorded via three channels, A, B, and C. Channel A transmitted data detected from a point of the duodenum approximately 2 cm from the pylorus, channel B, 10 cm from the pylorus, and channel C, 18 cm from the pylorus.

Dashed lines 141 show the propagation of the electrical activity from the pylorus toward the jejunum. Slow waves 140 are a low frequency feature of the duodenal electrical activity. In addition, bursting spikes 142 are high frequency and high amplitude features of the duodenal electrical activity.

Figure 2:
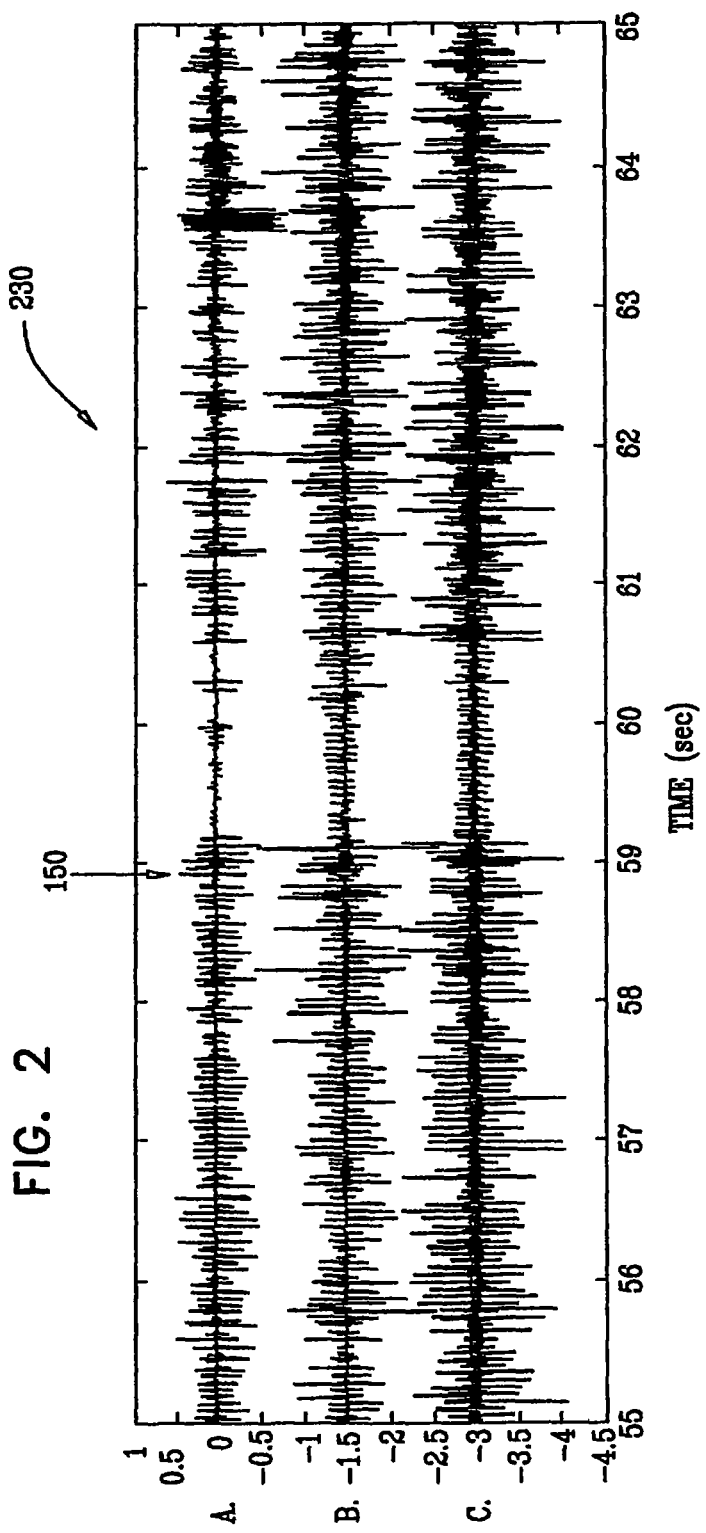
FIG. 2 is a graph illustrating duodenal electrical activity recorded in an eating pig, measured in accordance with an embodiment of the present invention.

Reference is now made to FIG. 2 which is a graph 230 illustrating duodenal electrical activity recorded in an eating pig, in accordance with an embodiment of the present invention. The pattern of electrical activity recorded through channels A, B and C undergoes a change shortly after time 150 when the pig starts eating, in the 59th minute. These results indicate that monitoring a subject's duodenal electrical activity provides an indication of whether the subject is eating.

Figure 3:
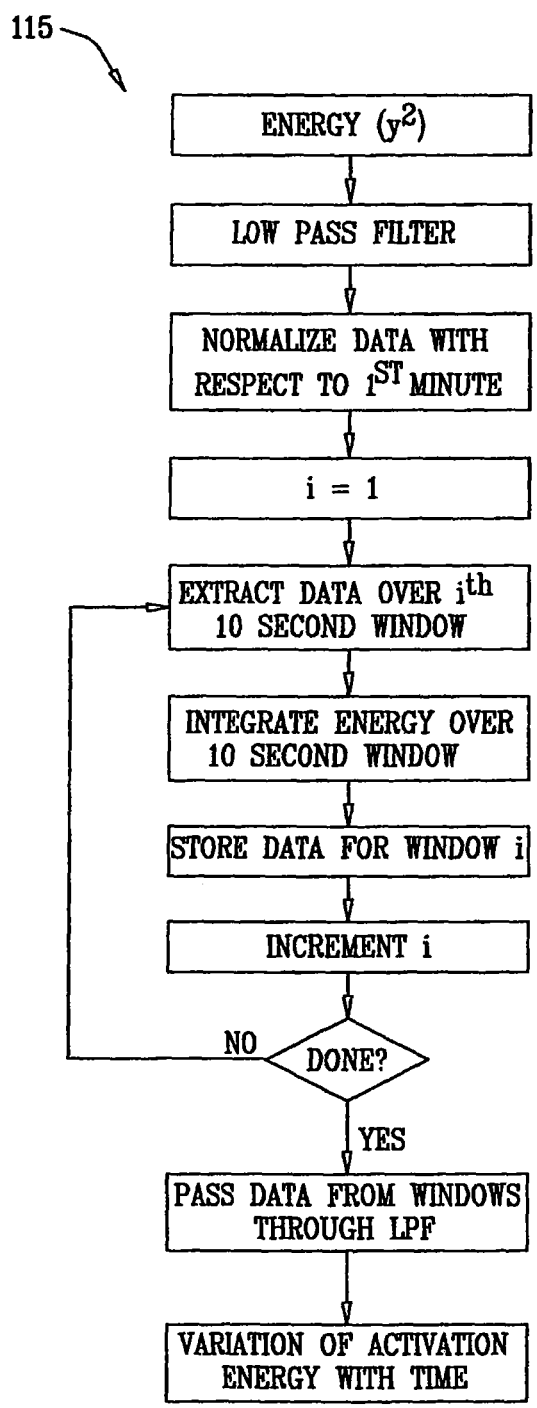
FIG. 3 is a flow chart of an algorithm used to determine the variation of duodenal activation energy with time, in accordance with an embodiment of the present invention.

Reference is now made to FIG. 3 which is a flow chart of an activation energy algorithm 115 used to determine the variation of duodenal activation energy with time, in experiments performed on pigs, in accordance with an embodiment of the present invention. Duodenal activation energy is defined as the integral of the square of the voltage recorded in the duodenum, over a given time window.

Duodenal activation energy may be defined as:

$$\int_{t_1}^{t_1+T} V^2 \, dt,$$

where V is the voltage recorded in the duodenum, the time window starts at time t1, and the duration of the time window is a length of time T. In some embodiments, duodenal activation energy is defined as the square of the current recorded in the duodenum integrated over the time window.

Running algorithm 115 yields a set of data which are the duodenal activation energies of respective 10 second time windows.

Running the algorithm on the voltage recorded in a pig duodenum comprises the following steps. The voltage is squared and is then passed through a low pass filter, to filter out high frequency components in the signal. Typically, the low pass filter filters out components of the recorded voltage having frequencies that are greater than 10 Hz. The data are then normalized with respect to the voltage recorded in the first minute. Normalization comprises dividing the energy by the maximum of squared voltage recorded in the first minute.

The data from the first ten seconds are extracted, and the squared voltage vs. time curve is integrated over 10 seconds, which yields the activation energy for the first 10 second window. This result is stored and the data of each of the subsequent 10 second windows are integrated.

Having performed the integration on all of the 10 second windows in the data set, there are stored a set of activation energies, each of the activation energies corresponding to a respective 10 second window. The set of activation energies is passed through a low pass filter, and a plot of the variation of duodenal activation energy with time is produced.

In some embodiments, algorithm 115 includes steps for determining the number of activations in each time window, the steps being generally similar to those described hereinbelow with reference to FIG. 6.

Figure 4:
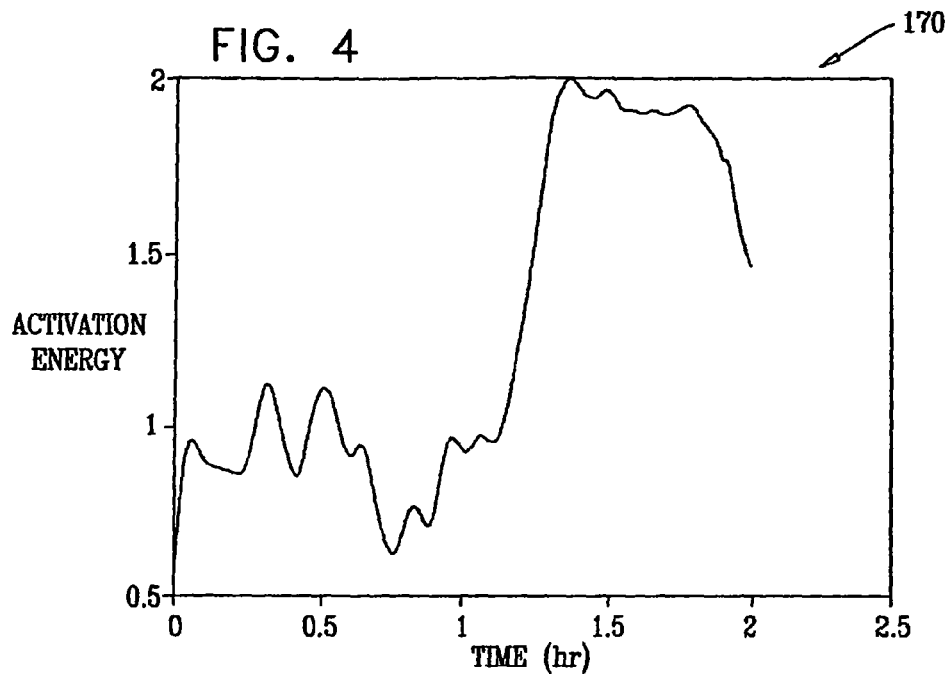
FIG. 4 is a graph illustrating the effect of eating on the recorded duodenal activation energy of pigs, calculated in accordance with an embodiment of the present invention.

Reference is now made to FIG. 4 which is a graph 170 of the effect of eating on the recorded duodenal activation energy of pigs, calculated in accordance with an embodiment of the present invention. Data were recorded via channel A of the duodenum, in a total of five experiments performed on three pigs. Algorithm 115 was applied to the data to produce graph 170 which is a plot of activation energy against time. The pigs started eating at 59 minutes. The large rise in the activation energy soon after the commencement of eating indicates that monitoring the activation energy of a subject's duodenum provides an indication of when the subject is eating.

Figure 5:
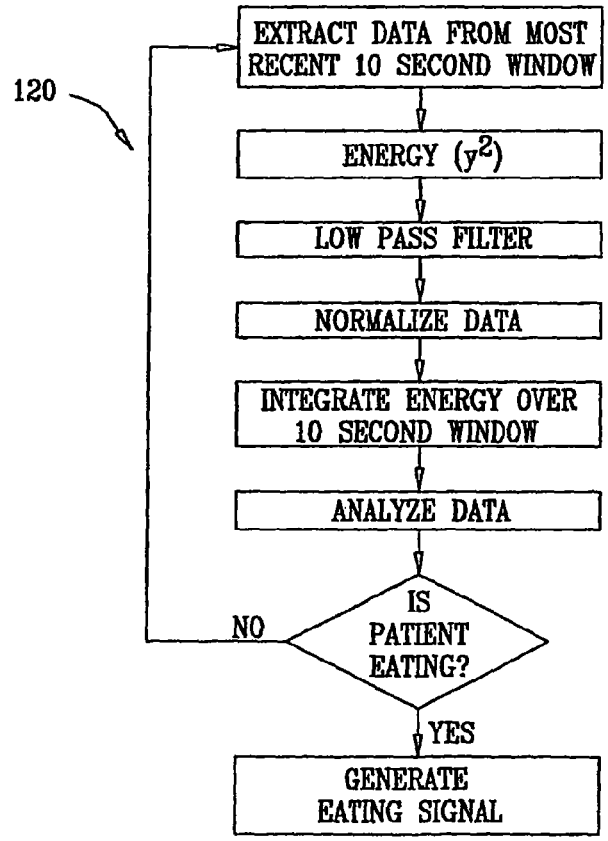
FIG. 5 is a flow chart of an algorithm used to determine if a subject is eating, in accordance with an embodiment of the present invention.

Reference is now made to FIG. 5, which is a flow chart of an activation energy algorithm 120 used to determine if a subject is eating, in accordance with an embodiment of the present invention. Algorithm 120 processes data recorded by an electrode disposed on the subject's duodenum. The algorithm calculates the activation energy of respective 10 second windows. It analyzes the activation energy of respective windows to determine whether the subject is eating.

In some embodiments, the 10 second windows are interleaved. For example, at 0 seconds the first 10 second window starts, at 5 seconds the second 10 second window starts, etc. Alternatively, each 10 second window begins as the previous 10 second window ends or after the previous 10 second window ends. For some applications, a window of a different length of time is used instead of a 10 second window, for example, a 5 second window, or a 20 second window.

Algorithm 120 extracts the last 10 seconds of data recorded by an electrode disposed on the duodenum of a subject. The recorded voltage is squared, passed through a low pass filter, and normalized. For example, before the algorithm is run, an electrode may be placed on the subject's duodenum, and the voltage is recorded for one hour. The maximum squared voltage in that hour is determined, and the algorithm normalizes data with respect to the maximum squared voltage.

The normalized squared voltage is then integrated over the 10 second window to yield the activation energy for the 10 second window. The data are analyzed to determine whether or not the subject is eating.

In some embodiments, the analysis comprises determining if the activation energy is greater than, or less than, a certain value. Alternatively or additionally, the activation energy of each window is analyzed with respect to that of the window or windows which precede it. The variation of the activation energy with time is analyzed to determine whether the subject is eating.

In some embodiments, algorithm 120 includes steps for determining the number of activations in each time window, the steps being generally similar to those described hereinbelow with reference to FIG. 6. The number of activations in each time window is analyzed to determine whether the subject is eating.

Figure 6:
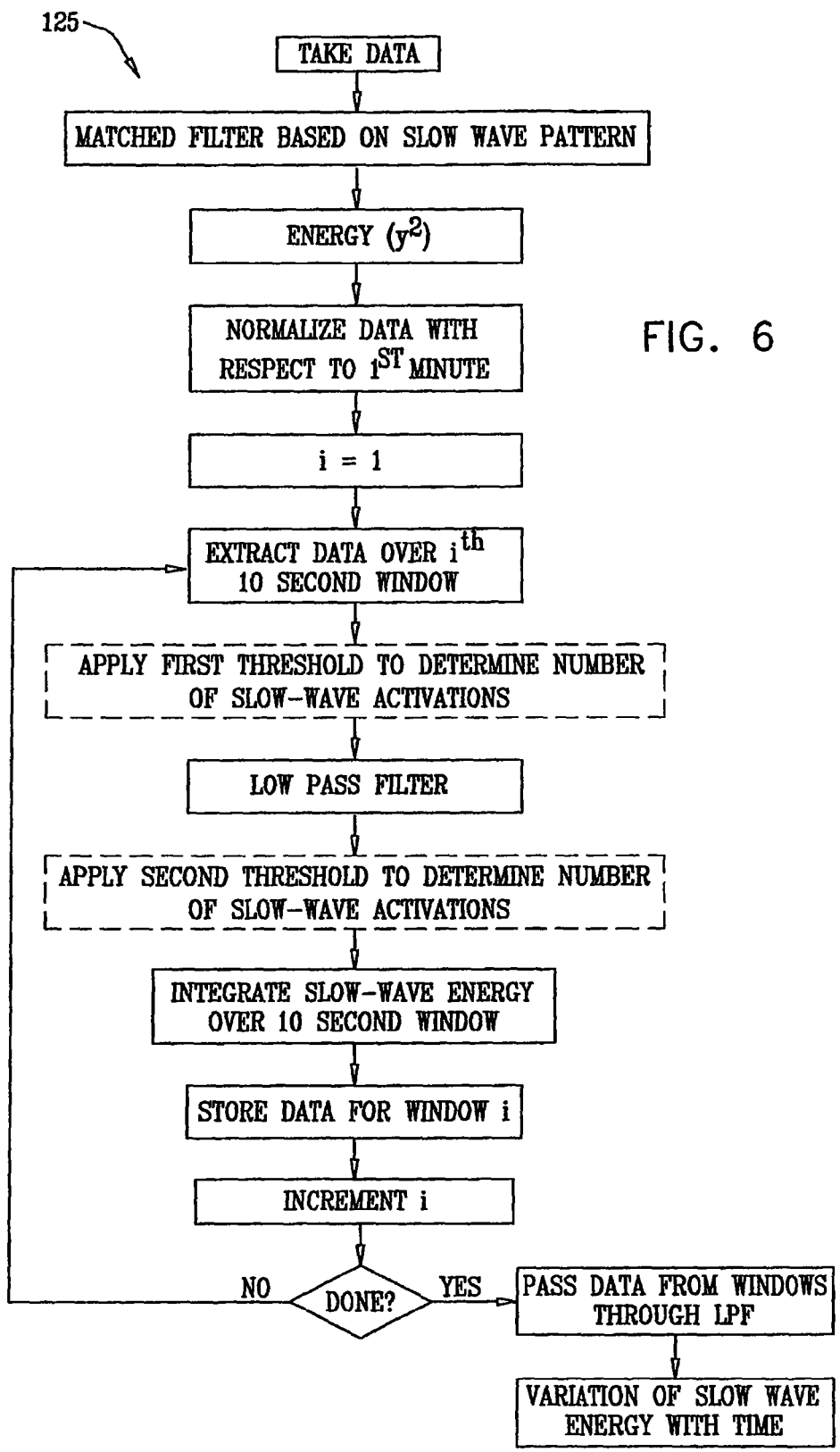
FIG. 6 is a flow chart of an algorithm used to determine the variation of duodenal slow wave energy with time, in accordance with an embodiment of the present invention.

Reference is now made to FIG. 6, which is a flow chart of a slow wave energy algorithm 125 used to determine the variation of duodenal slow wave energy with time, in experiments performed on pigs, in accordance with an embodiment of the present invention. Duodenal slow-wave energy is defined as the integral of the square of the voltage of the slow wave components of the duodenal electrical activity, over a given time window.

Duodenal slow wave energy may be defined as follows:

$$\int_{t_1}^{t_1+T} S^2 \, dt,$$

where S is the voltage of the duodenal slow waves, the time window starts at time t1, and the duration of the time window is a length of time T. In some embodiments, the duodenal slow-wave energy is defined as the square of the current of slow-wave components of duodenal electrical activity integrated over the time window.

The output of the algorithm is a set of data which show the variation of the duodenal slow wave energy with time.

Running the algorithm on the electrical energy recorded in the duodenum comprises the following steps. The data are passed through a matched filter based on a known slow wave pattern. The filter allows only voltage components which correspond to slow waves to pass through. The slow wave voltage spectrum is then squared and normalized with respect to the data recorded in the first minute.

The data from the first 10 seconds are extracted and passed through a first low pass filter. The squared slow wave voltage is integrated over the ten second window to give the slow wave energy of the window. The result for the first window is stored, and the steps are repeated on the subsequent windows. When the slow wave energy of all the windows has been found, the data from the windows are passed through a second low pass filter. The data from the windows are processed to produce a plot of the variation of slow wave energy with time.

In some embodiments, algorithm 125 includes steps (indicated by dashed boxes) for determining the number of slow-wave activations in each time window, i.e., the rate of slow wave activations. Each time window is divided into a number of periods, typically numbering between five and twenty. Periods in which the normalized squared voltage curve is greater than 10% of the squared voltage with respect to which the data were normalized are assigned a value of one. Periods in which the curve is less than 10% are assigned a value of zero. The number of slow-wave activations in the time window is defined as the number of periods in the time window that are assigned a value of one. In some embodiments, a different percentage is used as the threshold for determining the number of slow wave activations, for example, 5% or 15%.

In some embodiments, a second threshold is applied to the data of each 10 second window after the data have passed through the first low-pass filter, in order to identify the number of activations that are of sufficient time duration that they correspond to slow wave events. In the experiments which were conducted on pigs, the results of which are described hereinbelow, the first and second thresholds were different. Before passing through the low pass filter, periods were assigned a value of zero if the squared voltage curve was lower than 10%. The second threshold, which was applied after the filtering, assigned a value of zero to periods in which the squared voltage curve was lower than 5%.

Figure 7:
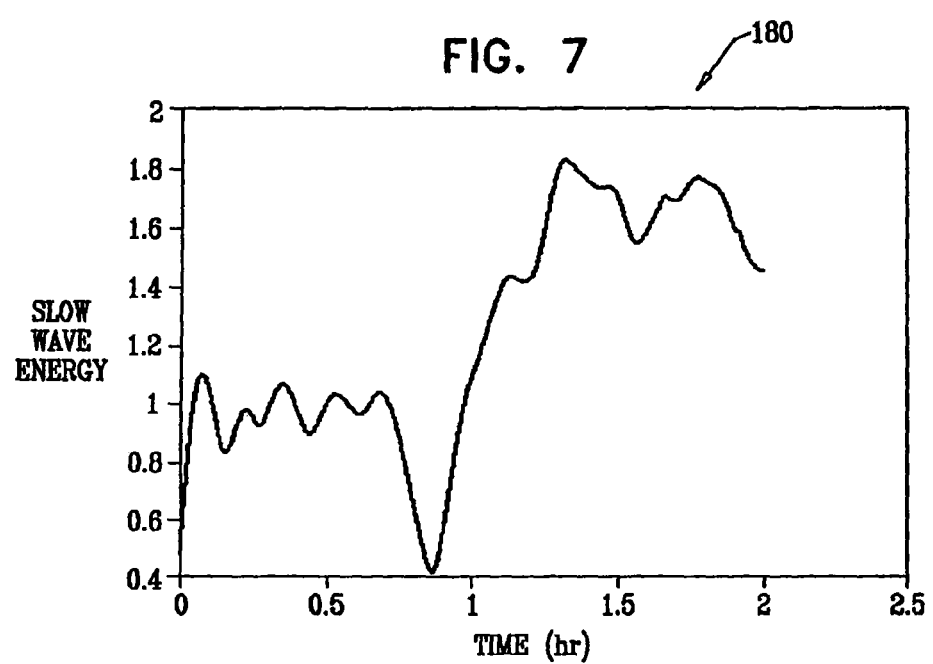
FIG. 7 is a graph illustrating the effect of eating on the recorded duodenal slow wave energy of pigs, calculated in accordance with an embodiment of the present invention.

Reference is now made to FIG. 7, which is a graph 180 illustrating the effect of eating on the recorded duodenal slow wave energy of pigs. Data were recorded via channel A of the duodenum, in a total of five experiments performed on three pigs. Algorithm 125 was applied to the data to produce graph 180, which is a plot of slow wave energy against time. The pigs started eating in the 59th minute, at which point there is a noticeable change in the slow wave energy curve. These results indicate that monitoring the slow wave energy of a duodenum of a subject provides an indication of whether the subject is eating.

Figure 8:
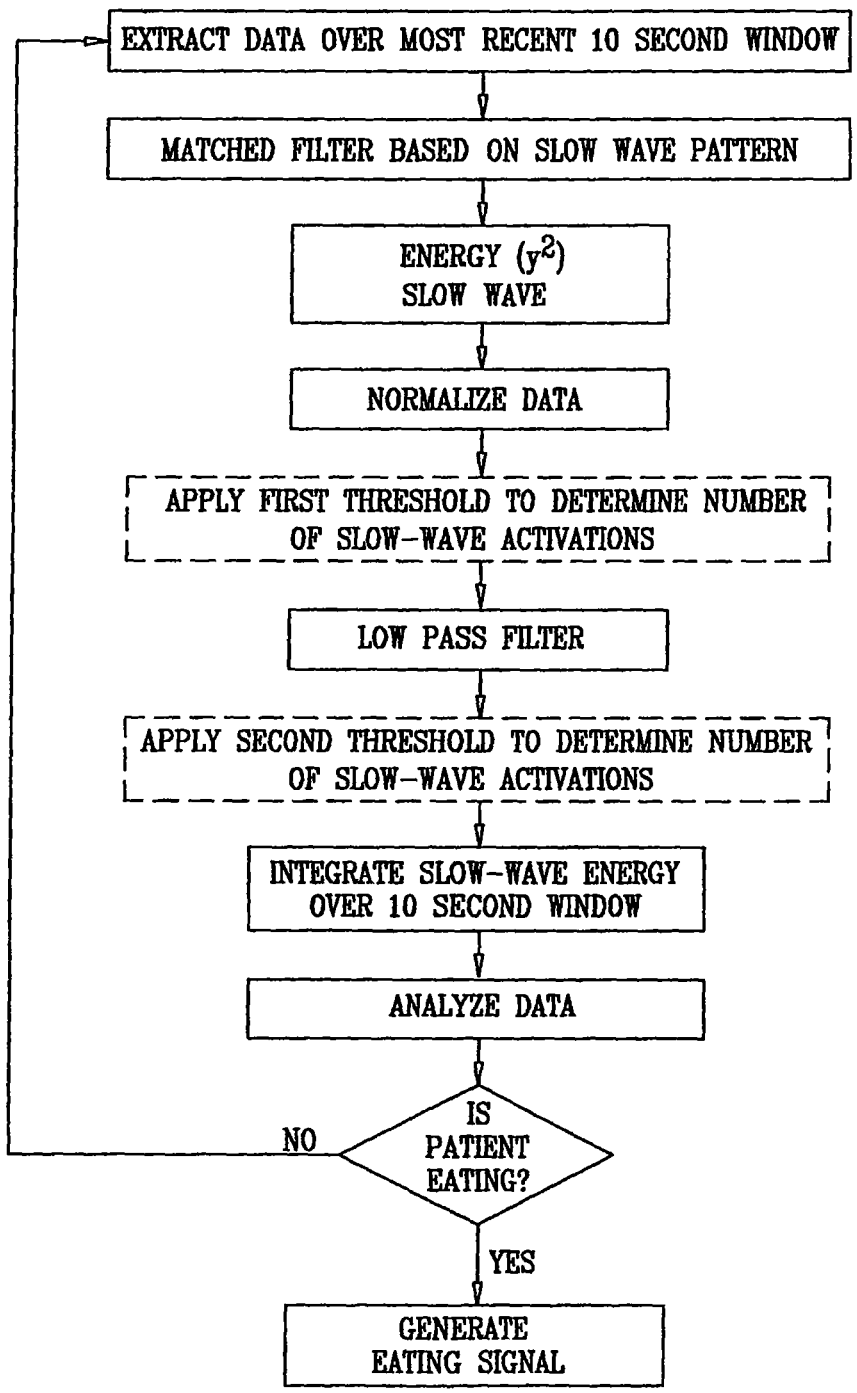
FIG. 8 is a flow chart of an algorithm used to determine if a subject is eating, in accordance with an embodiment of the present invention.

Reference is now made to FIG. 8, which is a flow chart of a slow wave energy algorithm 130 used to determine if a subject is eating, in accordance with an embodiment of the present invention. The algorithm determines if the subject is eating using slow wave energy data recorded by an electrode disposed on the subject's duodenum.

Data from the most recent time window recorded by a duodenal electrical energy sensor are extracted. The parameters of the time windows are generally similar to those described hereinabove with respect to algorithm 120. The data are passed through a matched filter which matches the data to a known slow wave pattern, and extracts only the data which correspond to slow waves. In some embodiments, the matched filter is configured to match the data to a previously recorded slow wave pattern of the subject.

The slow wave voltage is squared and normalized, in a generally similar manner to that described hereinabove, with reference to algorithm 120. The slow wave voltage data are passed through a first low pass filter to extract slow wave events and to remove noise. The squared slow wave voltage is then integrated over the 10 second window to find the slow wave energy of the window. The slow wave energy of the window is analyzed to determine if the subject is eating. In some embodiments, the energy is compared with a given value, and an indication of eating signal is generated if the slow wave energy exceeds that value, or if the slow wave energy is less than that value. Alternatively or additionally, the slow wave energy of the window is analyzed with respect to the slow wave energy of one or more of the preceding windows, to determine if the subject is eating.

In some embodiments, algorithm 130 includes steps (indicated by dashed boxes) for determining the number of slow-wave activations in each time window, i.e. the rate of slow wave activations. Algorithm 130 determines the number of slow-wave activations in a generally similar manner to that described hereinabove with reference to algorithm 125. In some embodiments, the number of slow wave activations in each time window is determined before the data are passed through the low-pass filter. Alternatively or additionally, the number of activations per time window is determined after the data have passed through the filter. In some embodiments, a duodenal eating sensor detects if the subject is eating by detecting the number of slow wave activations in each time window.

Figure 9:
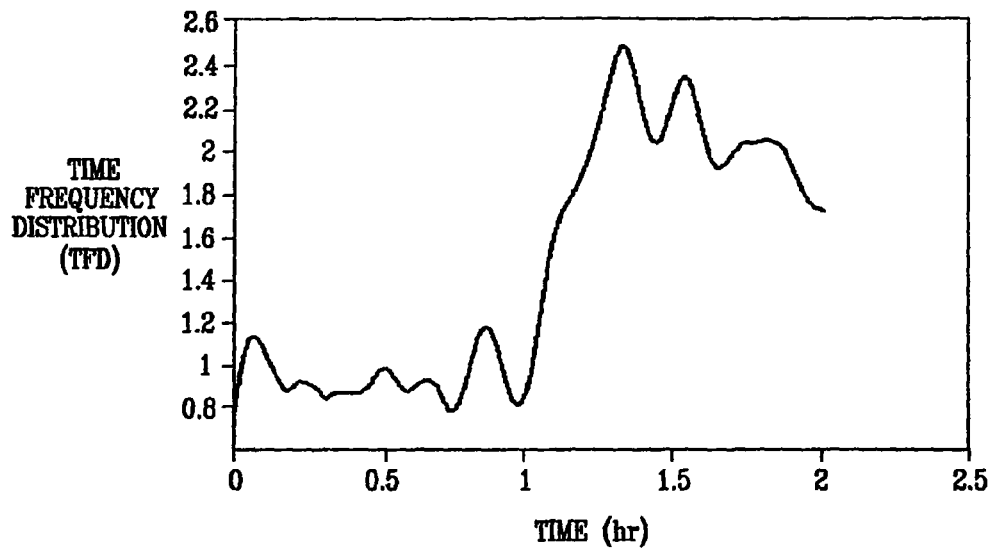
FIG. 9 is a graph illustrating the effect of eating on a time frequency distribution of the recorded duodenal slow waves of pigs, calculated in accordance with an embodiment of the present invention.

Reference is now made to FIG. 9, which is a graph 190 illustrating the effect of eating on a time frequency distribution of duodenal slow waves of pigs. Data were recorded via channel A of the duodenum, in a total of five experiments performed on three pigs. Graph 190 is a time frequency distribution of the recorded slow waves. Data from ten second time intervals were extracted and were operated on with Hamming windows, each window having 50% overlap with its adjacent windows. A fast Fourier transform using 256 time points of the resultant data was applied, and a number representative of the lower frequency components was calculated to yield the value of one time point in graph 190. Subsequently, the next ten second time interval was evaluated, to yield the value of the next time point in graph 190.

The number representative of the lower frequency components was calculated by summing the frequencies of spectral components in the low frequency range of 0 Hz to 25 Hz. In some embodiments, a number representative of the lower frequency components is calculated by summing the frequencies of spectral components in the frequency range 0 Hz to 50 Hz, or in the range 2 Hz to 12 Hz. In some embodiments, frequencies of spectral components that result from external interference or from interference unrelated to detecting eating are not included in the summation.

The pigs started eating in the 59th minute, following which there is a change in the pattern of the curve. These results indicate that monitoring the variation of the time frequency distribution of the slow wave energy with time provides an indication of whether a subject is eating.

Figure 10:
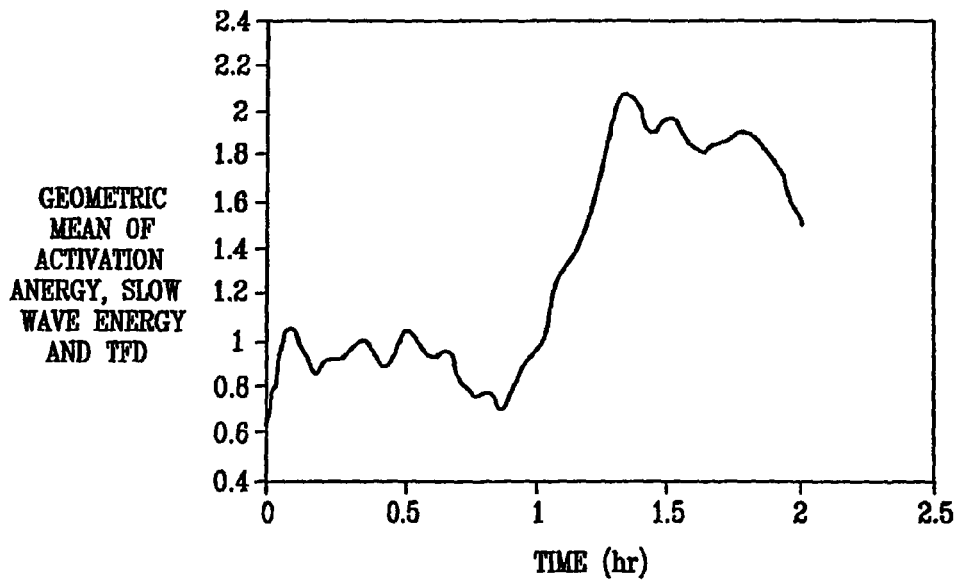
FIG. 10 is a graph illustrating the effect of eating on the geometric mean of the recorded duodenal activation energy, slow wave energy, and time frequency distribution of the slow wave energy of pigs, calculated in accordance with an embodiment of the present invention.

Reference is now made to FIG. 10, which is a graph of the effect of eating on a combined measure of the duodenal activation energy, slow wave energy, and time frequency distribution of the slow wave energy of pigs. Graph 200 is found by normalizing the curves from graphs 170, 180 and 190 with respect to each other, and calculating the geometric mean of these curves. The shape of the curve changes after 59 minutes, the time when the pigs started eating. These results indicate that monitoring the variation of a combined measure of the normalized slow wave energy, activation energy and time frequency distribution of the slow waves of a duodenum of a subject provides an indication of whether the subject is eating.

Reference is now made to FIG. 11, which is a graph 210 illustrating the effect of driving a current toward a pig's duodenum, measured in accordance with an embodiment of the present invention. Channels B and C recorded electrical activity in portions of a pig's duodenum which were respectively 10 cm and 18 cm from the pylorus. The graph shows the variation with time of electrical activity recorded through channels B and C. Arrows 160 indicate points in time when electrical current was driven via channel A toward a portion of the duodenum 2 cm from the pylorus. An alternating current was generated, comprising a biphasic square pulse train, in which each phase had an amplitude of 3.5 mA and a duration of 7 ms, and in which the overall frequency of the pulse train was 30 Hz (i.e., the time between the onset of successive biphasic pulses was about 33 ms). This biphasic pulse train was driven into the duodenum for 0.5 seconds, every 4 seconds. Stars 162 indicate bursting spikes recorded in portions B and C, which indicate that the driving of the current caused the duodenum to contract.

Figure 12A:
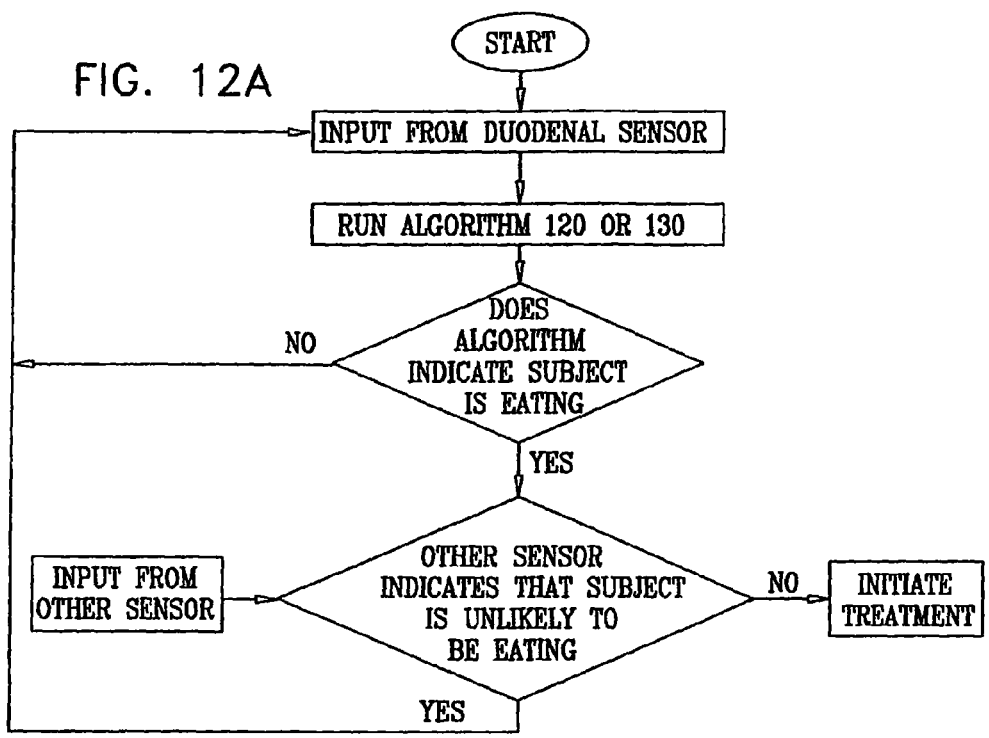
FIGS. 12A and 12B are schematic illustrations of the functions of a duodenal eating sensor control unit, in accordance with respective embodiments of the present invention.
Figure 12B:
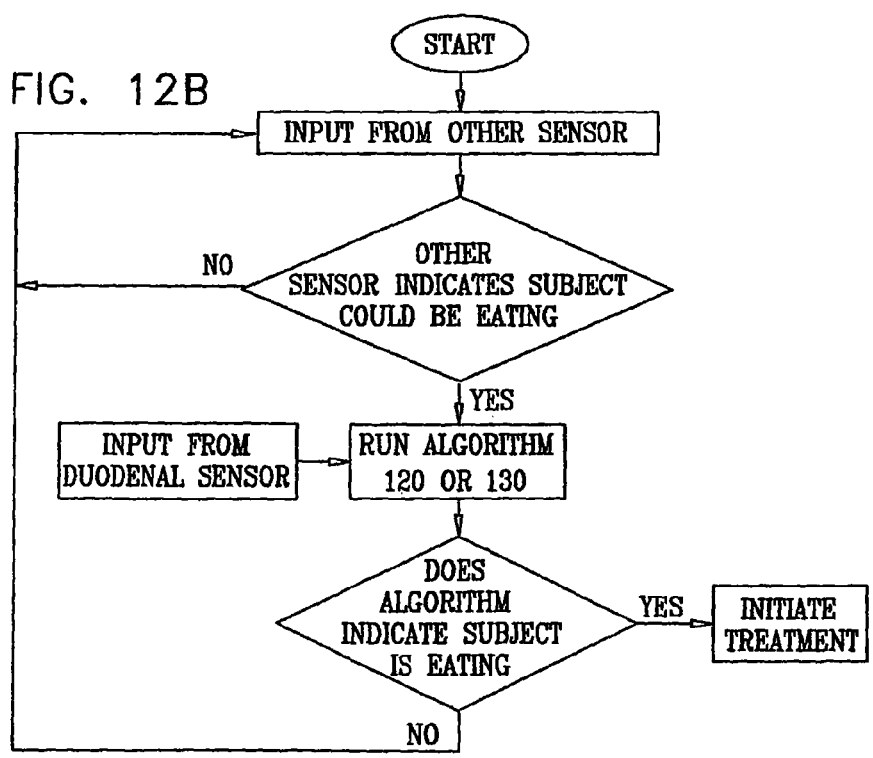

Reference is now made to FIGS. 12A and 12B, which are flow charts of the functions of a duodenal eating sensor control unit, in accordance with respective embodiments of the present invention. The duodenal eating sensor comprises an electrode disposed on the duodenum of the subject, and configured to detect electrical activity in the duodenum of the subject. In some embodiments, the apparatus comprises one or more additional sensors configured to detect indications that the subject is unlikely to be eating.

In some embodiments, the additional sensor comprises a respiration sensor configured to provide an indication that the subject is sleeping and is therefore unlikely to be eating. Alternatively or additionally, the additional sensor comprises an angle sensor configured to detect the angle at which the subject's body is disposed. If the subject is horizontal, for example, it may be an indication that the subject is sleeping, or is otherwise in a position in which the subject is unlikely to be eating.

Further alternatively or additionally, the sensor comprises a cardiac sensor configured to detect cardiac events of the subject and to withhold treatment responsively. For example, the treatment may only be initiated if the heart rate of the subject is between an upper and a lower threshold. If the heart rate of the subject exceeds the upper threshold, this indicates that the subject is exercising, and if the heart rate is below the lower threshold, it indicates that the subject is sleeping. Still further alternatively or additionally, the additional sensor comprises an acceleration sensor configured to withhold the treatment when the subject is apparently exercising or sleeping.

In some embodiments (FIG. 12A), the control unit is configured to receive data from the duodenal sensor. The control unit runs an algorithm to determine if the data from the duodenal electrodes indicate that the subject is eating. The algorithm determines the indication that the subject is eating based upon any one of a number of factors, or a combination thereof. The factors include, but are not limited to, duodenal activation energy, duodenal slow wave energy, the time frequency distribution of the duodenal slow waves, and/or the rate of slow wave activations. Typically, the control unit runs algorithm 120 or 130, as described hereinabove, to determine if the subject is eating.

If the subject is not eating, the control unit is configured to continue receiving the data from the eating sensor and running the algorithm to determine if the subject is eating. If the input from the duodenal sensor indicates that the subject is eating, the control unit is configured to receive an input from the additional sensor. If the additional sensor indicates that the subject is unlikely to be eating, because, for example, the subject is sleeping, the indication from the additional sensor overrides the indication from the duodenal sensor. The control unit is configured to continue receiving the data from the eating sensor and running the algorithm to determine if the subject is eating. If the duodenal sensor indicates that the subject is eating and the additional sensor indicates that the subject may be eating, the control unit is configured to initiate a treatment of the subject.

In alternative embodiments (FIG. 12B), the control unit first receives input from the additional sensor. If the additional sensor indicates that the subject is unlikely to be eating, then the control unit continues to receive input from the additional sensor to determine if the subject may be eating. If the additional sensor indicates that the subject may be eating, the control unit is configured to receive input from the duodenal sensor.

The control unit runs an algorithm to determine if the subject is eating, based on the input from the duodenal sensor, the algorithm being generally similar to that described hereinabove. If it is determined that the subject is not eating, the control unit continues to receive input from the additional sensor to determine if the subject may be eating. If it is determined that the subject is eating based on the data from the duodenal sensor, then a treatment of the subject is initiated.

The embodiment shown in FIG. 12B is typically (but not necessarily) practiced if it is determined that the eating detection algorithm uses a significant amount of battery power, and if it is desired to minimize the total amount of time that the eating detection algorithm is executed.

Figure 13:
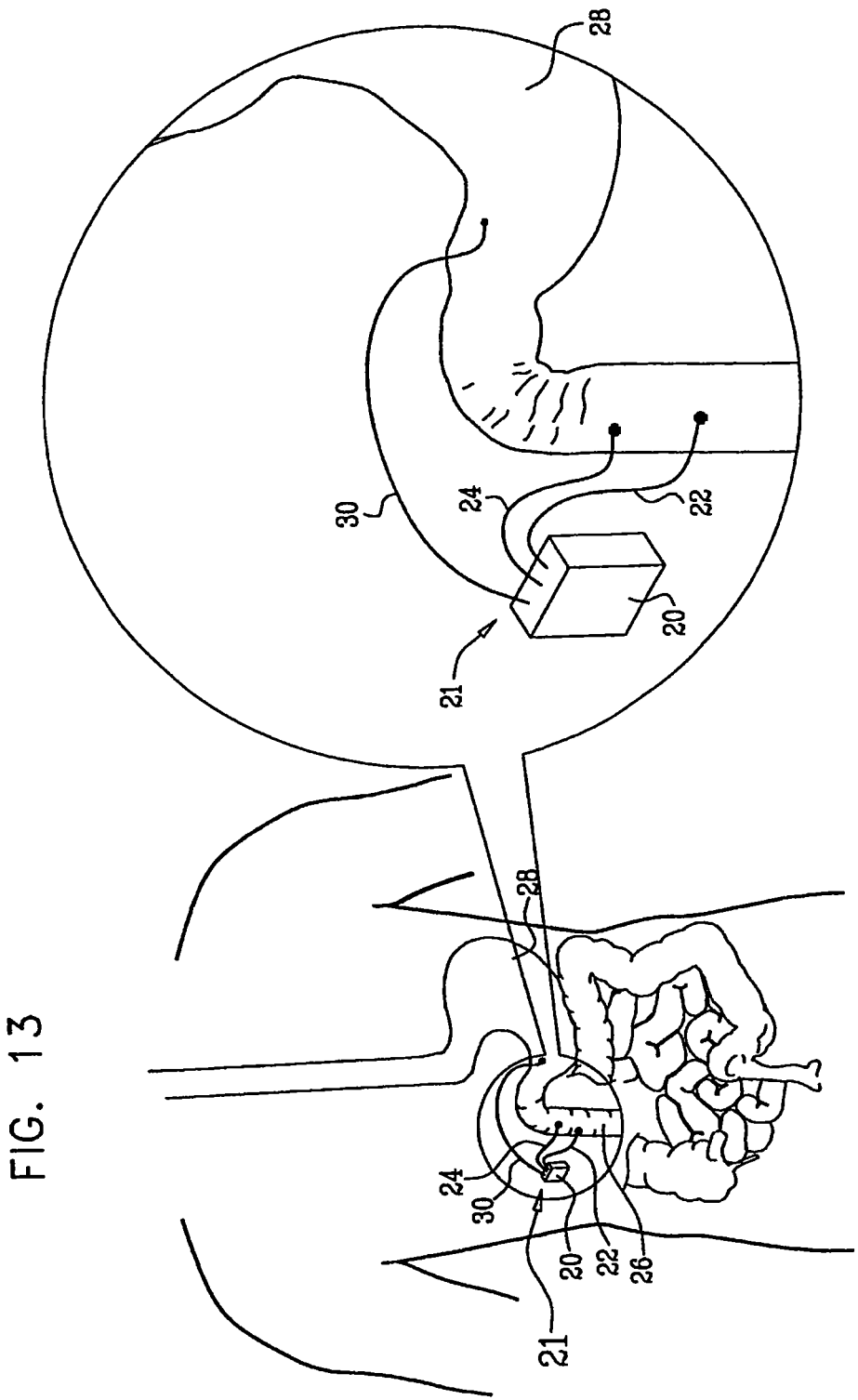
FIG. 13 is a schematic illustration of apparatus configured to drive current toward a subject's stomach, in accordance with an embodiment of the present invention.

Reference is now made to FIG. 13, which is a schematic illustration of implantable apparatus 21 configured to detect electrical activity of a duodenum 26 of a subject and to drive current toward the subject's stomach 28, in accordance with an embodiment of the present invention.

Apparatus 21 comprises a control unit 20 and a sensing electrode 22. In some embodiments, the apparatus comprises a second sensing electrode 24, and/or a treatment electrode 30. Sensing electrodes 22 and 24 are configured to detect electrical activity of duodenum 26 of the subject. Control unit 20 analyzes the electrical activity of the duodenum, as described hereinabove, to determine if the subject is eating. In some embodiments, the control unit comprises an additional sensor that detects indications that the subject is unlikely to be eating, as described hereinabove. For example, the additional sensor may include a respiration sensor, an acceleration sensor, an angle sensor, and/or a cardiac sensor. The control unit analyzes the electrical activity of the duodenum as well as data from the additional sensor, as described hereinabove, to determine if the subject is eating.

In some embodiments, if the subject is eating, the control unit is configured to drive a current into the subject's stomach via treatment electrode 30.

In some embodiments, control unit 20 is configured to regulate gastric motility by driving the current toward the stomach. For example, increasing the gastric motility allows less time for ingested food to be digested, which in turn decreases absorption of the food into the subject's body. Alternatively, decreasing the gastric motility causes the food to remain in the stomach and induces a feeling of satiety.

In some embodiments, control unit 20 is configured to modulate tension in the gastric wall by driving the current toward the stomach.

For some applications, control unit 20 is configured to cause the pylorus of the subject to close by driving the current into the stomach. Alternatively or additionally, the pylorus is caused to close by driving a current into a different location in the subject's body (e.g., a nerve innervating the pylorus, or a site on the duodenum). Further alternatively or additionally, apparatus 21 is configured to close the pylorus mechanically, in response to a detection that the subject is eating.

Figure 14:
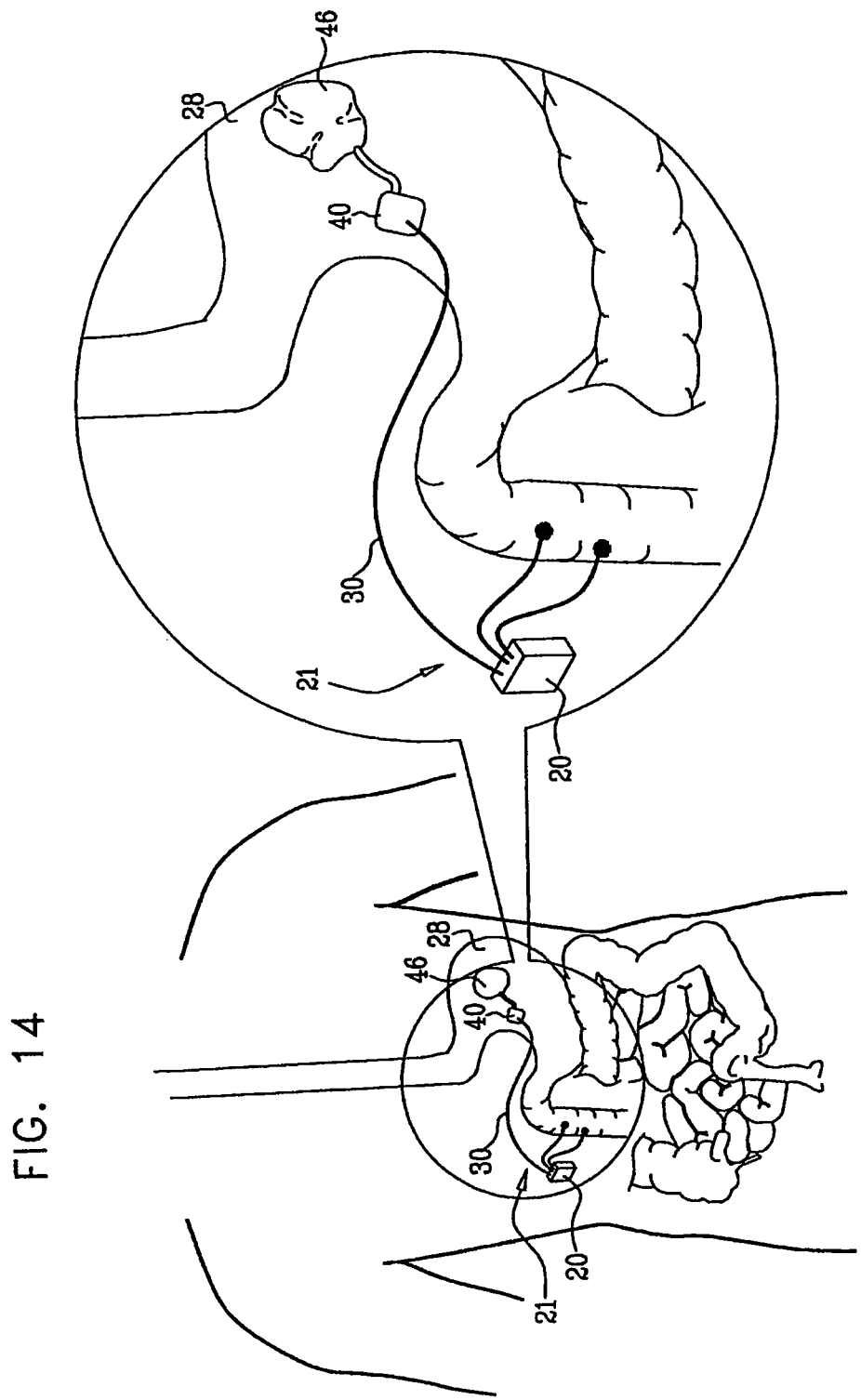
FIG. 14 is a schematic illustration of apparatus configured to inflate a balloon inside a subject's stomach, in accordance with an embodiment of the present invention.

Reference is now made to FIG. 14, which is a schematic illustration of implantable apparatus 21 configured to inflate a balloon inside the subject's stomach, in accordance with an embodiment of the present invention. In response to a detection that the subject is eating (e.g., using techniques described hereinabove), apparatus 21 drives a current toward an inflation device 40. The current causes inflation device 40 to inflate a balloon 46, disposed within the subject's stomach. In all other aspects, apparatus 21 is generally as described hereinabove.

Figure 15:
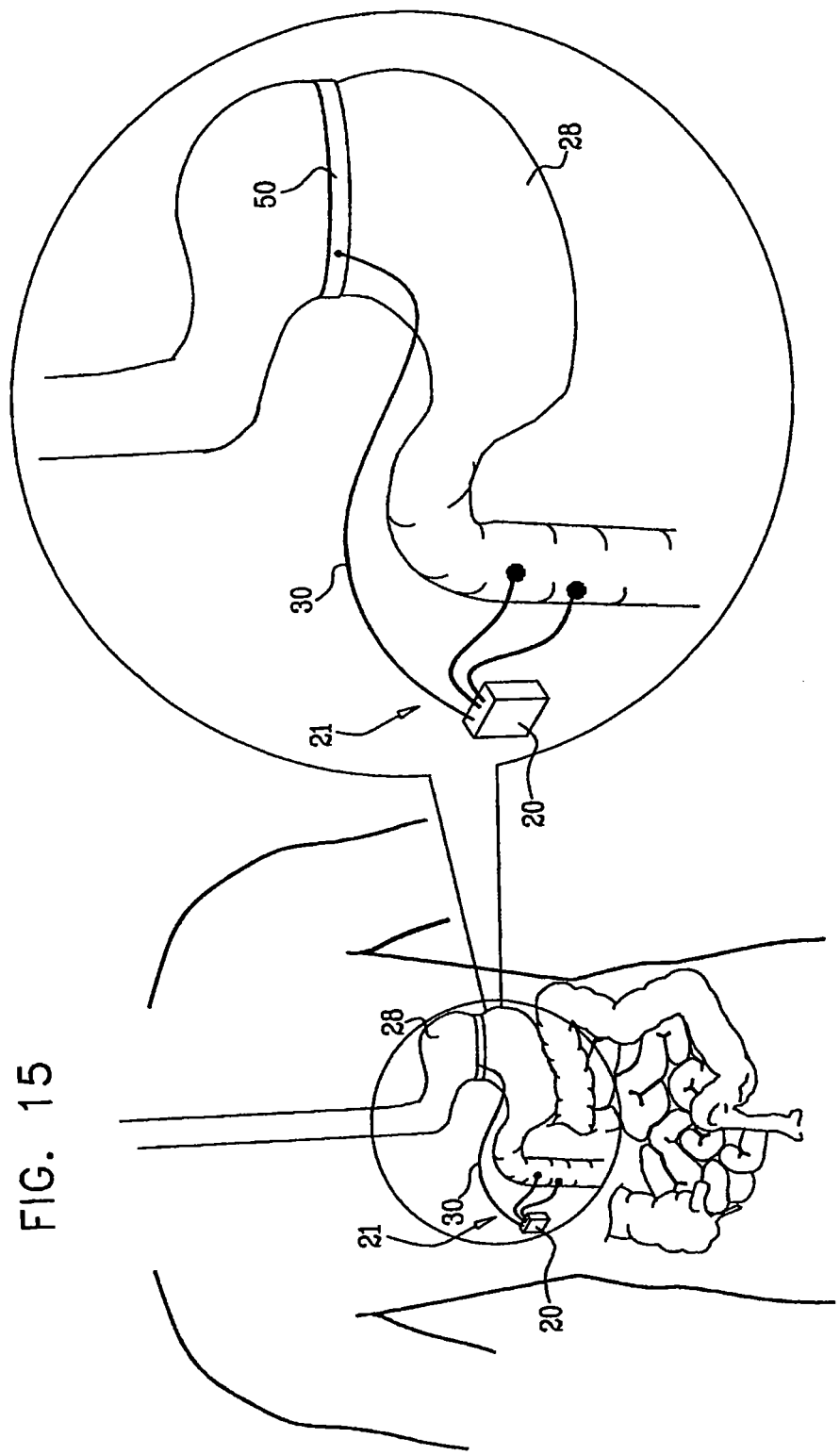
FIG. 15 is a schematic illustration of apparatus configured to tighten a band around a subject's stomach, in accordance with an embodiment of the present invention.

Reference is now made to FIG. 15, which is a schematic illustration of implantable apparatus 21 configured to tighten an adjustable band 50 around the subject's stomach, in accordance with an embodiment of the present invention. In response to a detection that the subject is eating, apparatus 21 is configured regulate an adjustable band 50 which is disposed around the subject's stomach. The current causes the adjustable band to tighten and constrict the stomach. In other aspects, apparatus 21 is generally as described hereinabove.

Figure 16:
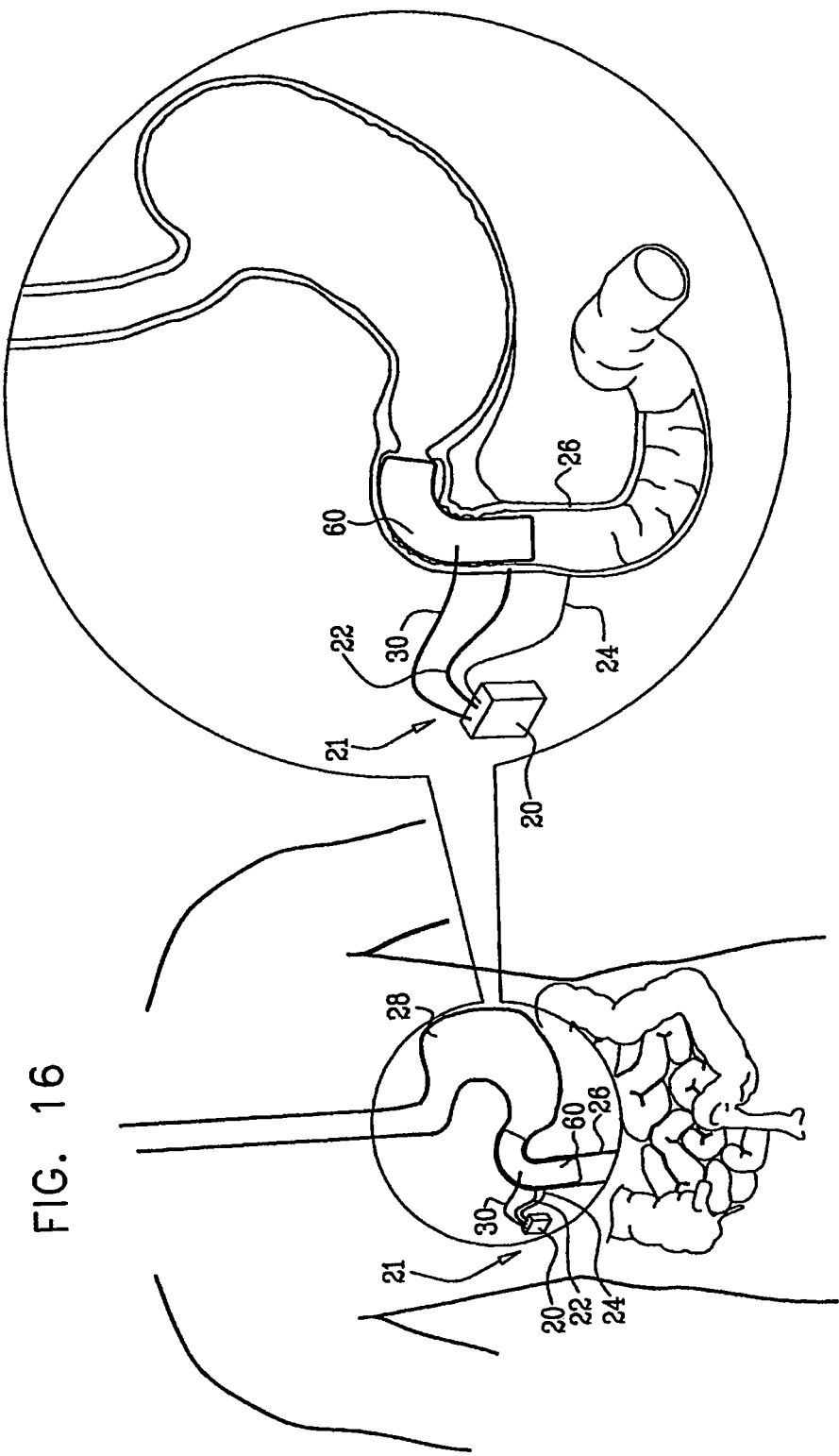
FIG. 16 is a schematic illustration of a duodenal eating sensor coupled to a duodenal sheath, in accordance with an embodiment of the present invention.

Reference is now made to FIG. 16, which is a schematic illustration of implantable apparatus 21 coupled to a duodenal sheath 60, in accordance with an embodiment of the present invention. Sheath 60 is configured to be disposed within the duodenum such that food, passing through the duodenum, passes via the sheath. In response to a detection that the subject is eating, control unit 20 drives a current toward the sheath to regulate the permeability of the sheath. In other aspects, apparatus 21 is generally as described hereinabove.

Figure 17:
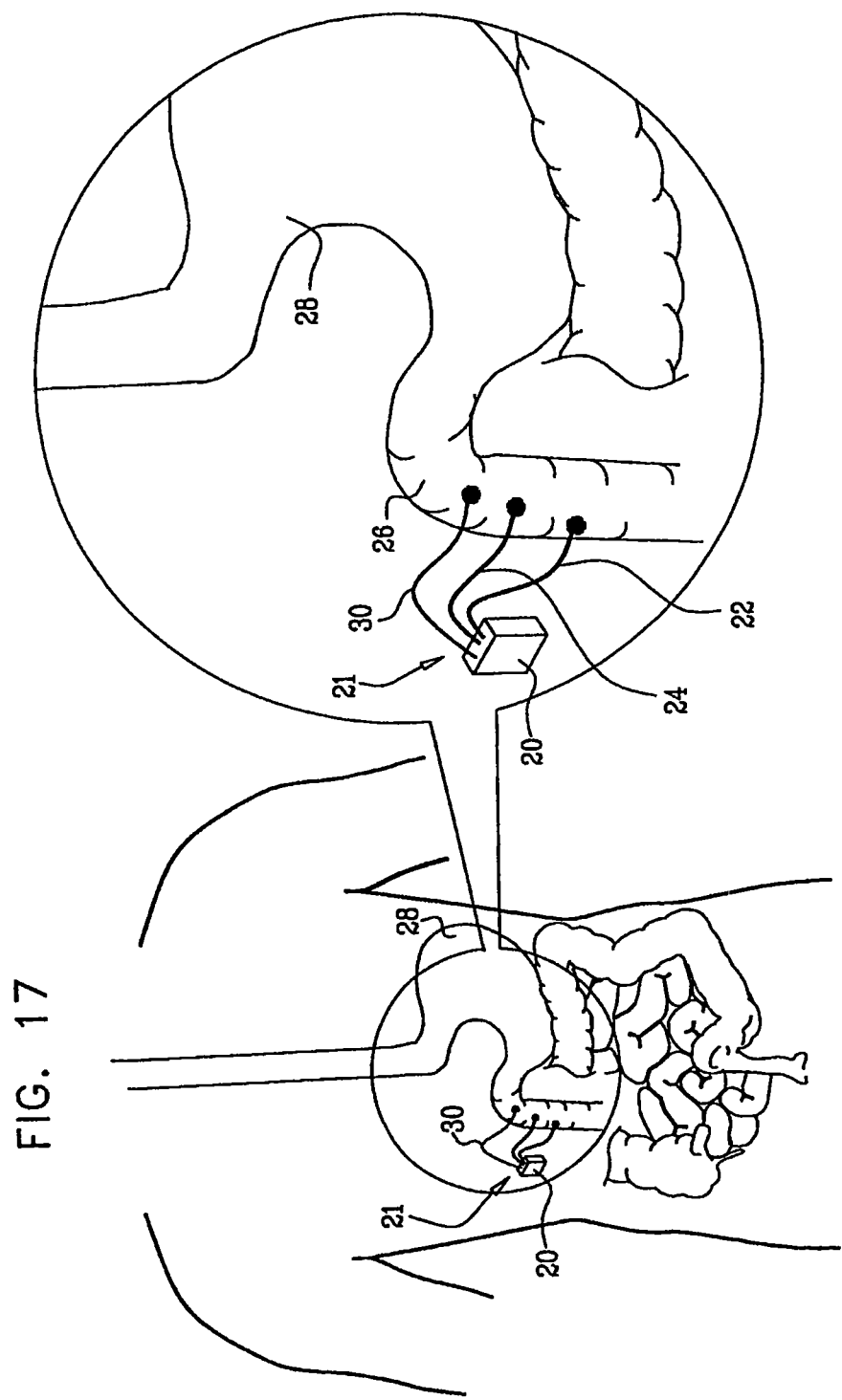
FIG. 17 is a schematic illustration of apparatus configured to regulate intestinal motility, in accordance with an embodiment of the present invention.

Reference is now made to FIG. 17, which is a schematic illustration of implantable apparatus 21 configured to regulate intestinal motility, and/or intestinal permeability, in accordance with an embodiment of the present invention. In response to a detection that the subject is eating, control unit 20 is configured to drive a current into the duodenum of the subject. Driving the current into the duodenum causes electrical activity in the duodenum, as described hereinabove with reference to FIG. 11, and resultant mechanical contractions. In some embodiments, the control unit drives the current into the duodenum via sensing electrode 22 and/or 24. Alternatively or additionally, the control unit drives the current via treatment electrode 30.

In some embodiments, intestinal motility is increased, to decrease the absorption of food through the duodenum. Alternatively, intestinal motility is decreased, to increase absorption of food through the duodenum due to the increased time in which the food is in the duodenum. For example, intestinal motility may be decreased to treat a malnourished subject. Alternatively or additionally, control unit 20 modulates intestinal permeability (for example, increases or decreases intestinal permeability) by driving the current into the duodenum.

For some applications, a pharmaceutical is administered to the subject when the subject eats. Apparatus 21 decreases intestinal motility in response to detecting that the subject is eating, which increases the absorption of the pharmaceutical through the duodenum.

Figure 18:
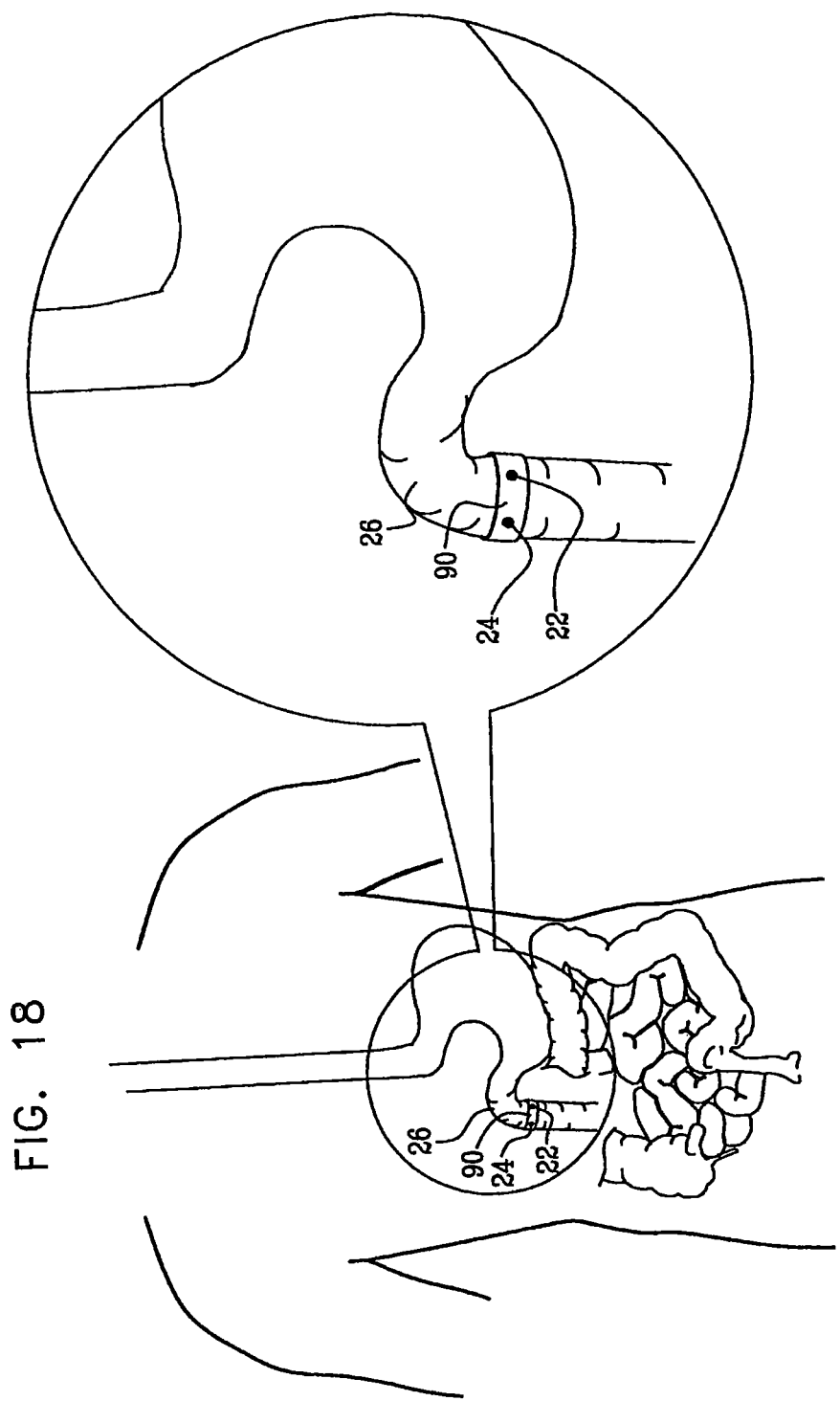
FIG. 18 is a schematic illustration of a plurality of duodenal electrodes implanted outside the duodenum, in accordance with an embodiment of the present invention.

Reference is now made to FIG. 18, which is a schematic illustration of a plurality of duodenal electrodes 22 and 24, implanted outside a duodenum 26, in accordance with an embodiment of the present invention. Typically, electrodes 22 and 24 are configured to detect duodenal electrical activity, as described hereinabove.

The electrodes are coupled to a ring 90. Typically, the electrodes are coupled to the duodenum by placing the ring around the outside of the duodenum. In an embodiment, the ring is implanted laparoscopically. Alternatively, the ring is inserted endoscopically.

Figure 19:
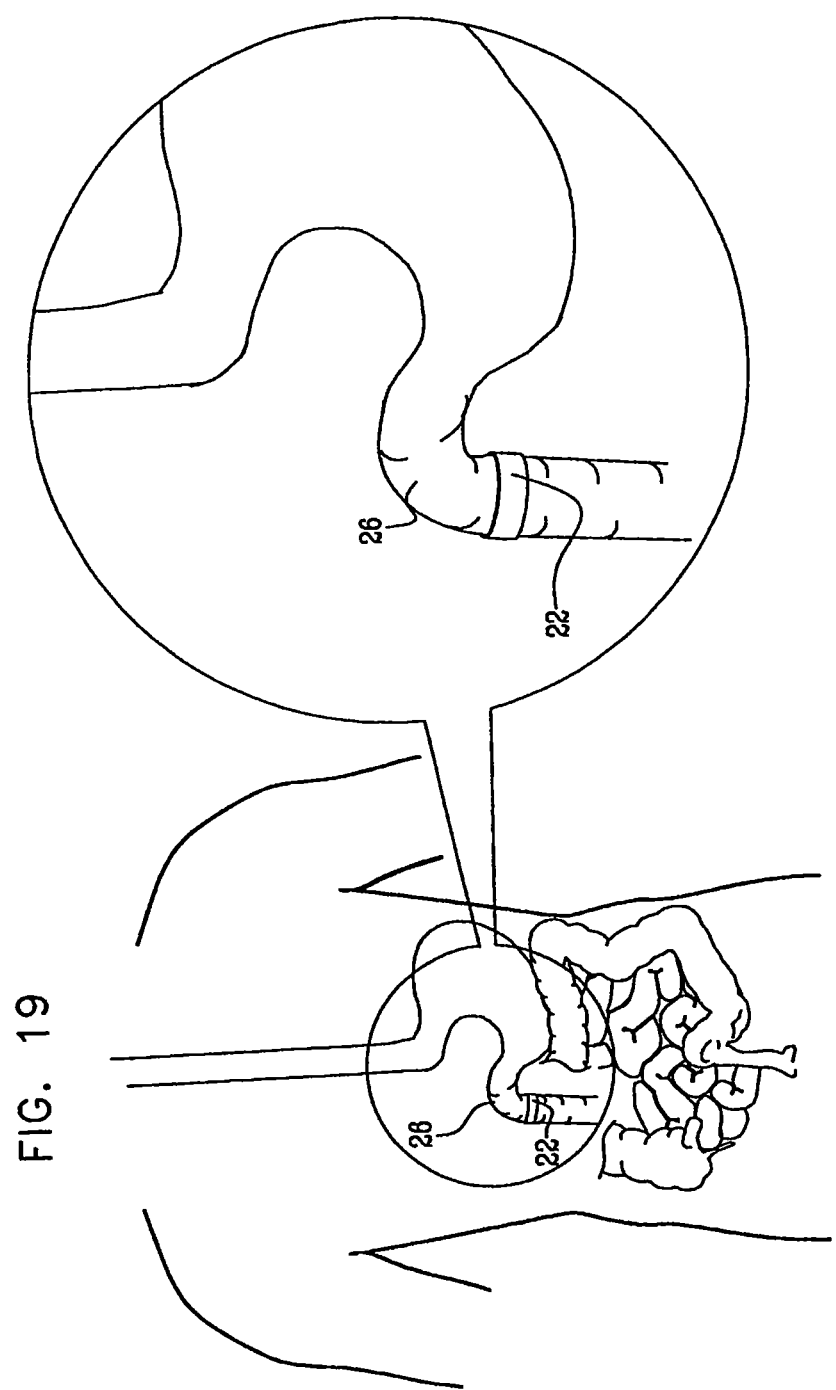
FIG. 19 is a schematic illustration of a duodenal ring electrode implanted outside the duodenum, in accordance with an embodiment of the present invention.

Reference is now made to FIG. 19, which is a schematic illustration of a duodenal ring electrode 22 implanted outside a duodenum 26, in accordance with an embodiment of the present invention. Typically, electrode 22 is configured to detect electrical activity of the duodenum, as described hereinabove.

The ring is coupled to the duodenum by placing the ring around the outside of the duodenum. In an embodiment, the ring is implanted laparoscopically. Alternatively, the ring is inserted endoscopically.

In some embodiments, electrode 24 also comprises a ring electrode. Alternatively, electrode 24 has a different shape.

Figure 20:
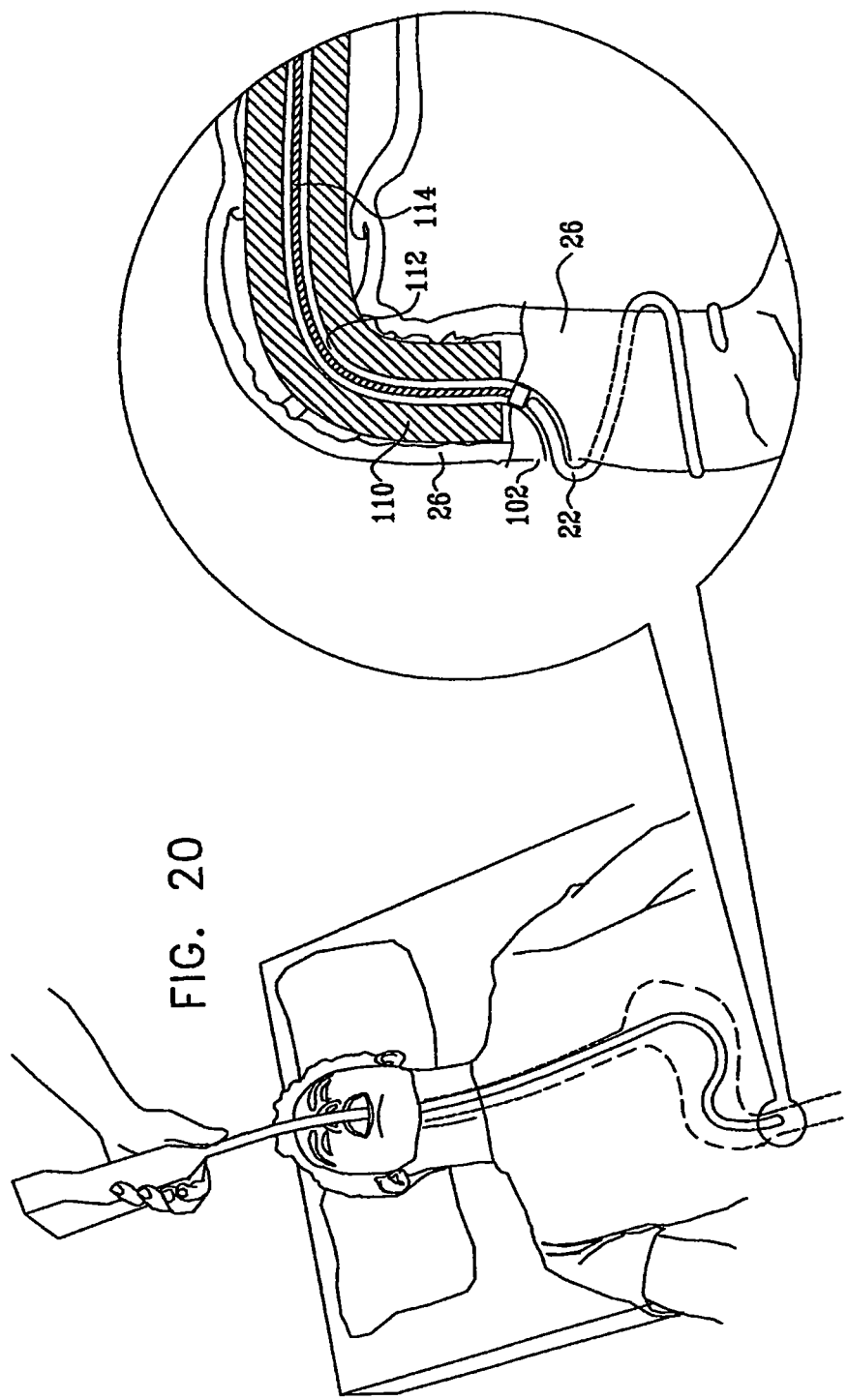
FIG. 20 is a schematic illustration of a helical electrode being implanted around the outside of the duodenum, in accordance with an embodiment of the present invention.

Reference is now made to FIG. 20, which is a schematic illustration of a helical electrode 22 being implanted around the outside of duodenum 26, in accordance with an embodiment of the present invention. Typically electrode. 22 is configured to detect electrical activity of the duodenum, as described hereinabove.

The helical electrode is typically implanted according to the following implantation procedure. A catheter 110 comprising a tube 112 is inserted into the duodenum. Electrode 22 is disposed within tube 112, its shape constricted by the dimensions of the tube. The electrode typically comprises a shape memory alloy such as nitinol, and is configured to assume a helical shape when it is not constricted.

A hole 102 is made in a wall of duodenum 26, using an incision tool, for example, the distal end of tube 112. The distal end of tube 112 is guided to hole 102. Alternatively, the distal end of tube 112 creates hole 102. A pushing element 114 pushes electrode 22 out of tube 112 and through hole 102. The electrode assumes a helical shape as it advances through hole 102, and the electrode wraps itself around the duodenum to complete the implantation procedure.

Figure 21:
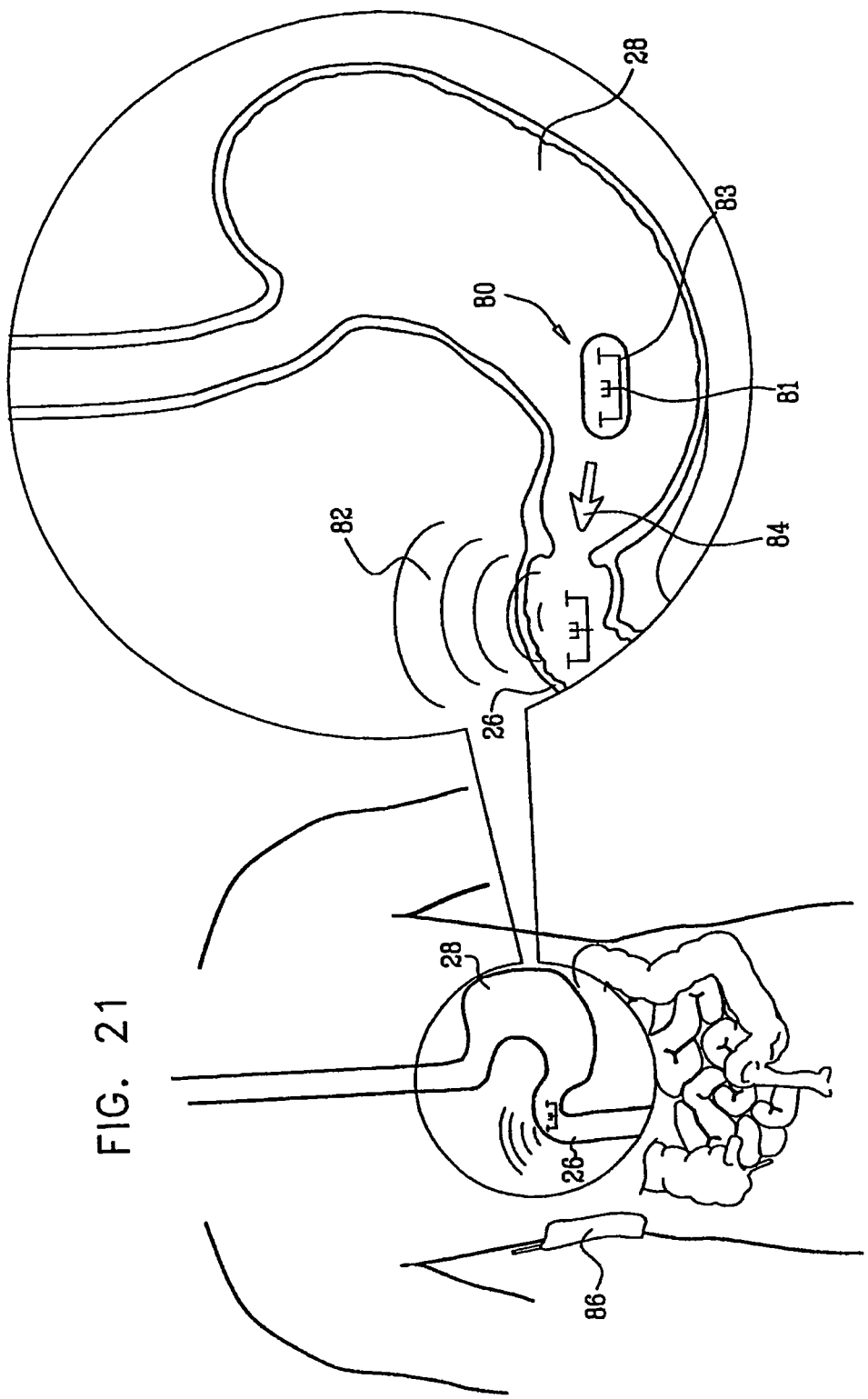
FIG. 21 is a schematic illustration of a duodenum-sensitive capsule passing into the duodenum, in accordance with an embodiment of the present invention.

Reference is now made to FIG. 21, which is a schematic illustration of a duodenum-sensitive capsule 80, in accordance with an embodiment of the present invention. The capsule typically comprises a duodenum sensitive coating 81 and a signal transmitter 83. The transmitter comprises an electrical circuit which is open while the transmitter is coated with coating 81.

The capsule passes through a subject's stomach 28 without coating 81 becoming dissolved. The capsule passes into the duodenum, in the direction shown by arrow 84, where the coating dissolves. The electrical circuit of the transmitter is closed by the flow of ions in the duodenum, and the transmitter begins to transmit signals 82, e.g., RF signals.

A detector 86, which is typically outside the subject's body, determines that the capsule has entered the duodenum by detecting signals 82. In some embodiments, the detector comprises a patch configured to be placed on the subject's body, or on the subject's clothes.

In some embodiments, a plurality of capsules 80 are administered to the subject. Typically, the transmitter of each of the plurality of capsules is configured to transmit a characteristic signal. In some embodiments, detector 86 is configured to analyze the detected signals to determine a characteristic of the gastrointestinal tract of the subject, such as the gastric emptying half time. For example, if ten capsules 80 are swallowed, the detector can identify the time until five of the capsules have entered the duodenum as the gastric emptying half time.

Reference is now made to FIG. 22, which is a graph 240 of electrical activity recorded in a pig's duodenum, in accordance with an embodiment of the present invention. Graph 240 is a plot of the raw voltage that was recorded in the duodenum, no data processing having been applied to the recorded voltage. At 35 minutes, a line 242 is marked on the graph indicating that food was administered to the animal at this point.

Reference is now made to FIG. 23, which is a graph 250 showing the geometric mean of (a) the duodenal activation energy and (b) the number of activations per unit time, where (a) and (b) are calculated based on the electrical activity of graph 240, in accordance with an embodiment of the present invention. The activation energy was determined by applying algorithm 115 (described with reference to FIG. 3) to the raw data that is shown in graph 240 (described with reference to FIG. 22). The number of activations per unit time was determined by processing the data of graph 240 using techniques similar to the steps indicated by the dashed lines of algorithm 125 (described with reference to FIG. 6). (The steps of algorithm 125 indicated by the dashed lines are for determining the number of slow-wave activations per unit time. In the data processing that was used to generate graph 250, the number of activations per unit time was determined even with respect to activations which did not correspond to slow-wave activations. Generally, the techniques for generating the data regarding the number of activations per unit time were similar to those described with respect to algorithm 125.) The geometric mean of the activation energy and the number of activations per unit time in the electrical activity was determined and is plotted in graph 250.

At about 35 minutes, line 242 is marked on the graph indicating that food was administered to the animal at this point. Overlaid on the plot of the geometric mean, in the region of line 242, is a characteristic pattern 254. The inventors hypothesize that the activation energy curve adopts a characteristic pattern around the time when a subject eats, the characteristic pattern being similar to pattern 254. The characteristic pattern is typically v-shaped, as shown, and lasts for more than five, e.g., more than ten, minutes. As shown, the characteristic pattern is demonstrated using less than 50 minutes of data.

Figure 24:
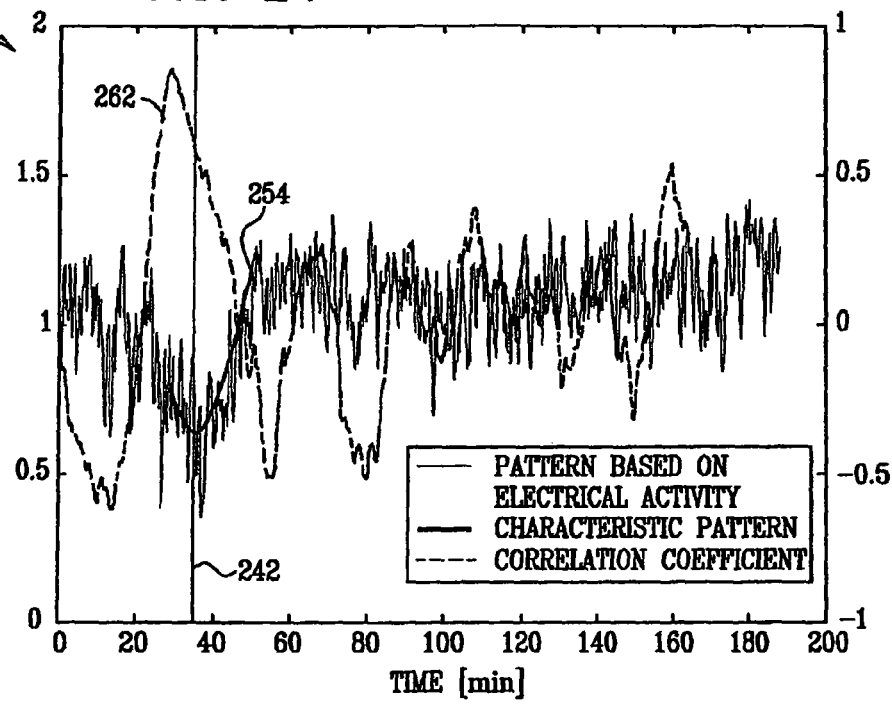
FIG. 24 is a graph including a cross-correlation coefficient curve showing a cross-correlation of the curve of FIG. 23 to a characteristic pattern, in accordance with an embodiment of the present invention.

Reference is now made to FIG. 24, which is a graph 260 showing the geometric mean curve of FIG. 23, as well as a cross-correlation coefficient (dashed) curve 262 showing a cross-correlation of the geometric curve to characteristic pattern 254, in accordance with an embodiment of the present invention. The cross-correlation coefficient is indicative of the level of correlation between the pattern of the geometric mean curve and characteristic pattern 254. The cross-correlation coefficient is calculated using standard techniques for calculating a cross-correlation coefficient of two data series. It may be observed that around 35 minutes, when food was administered to the animal, there is a high degree of correlation between the activation energy curve and the characteristic pattern.

Figure 25:
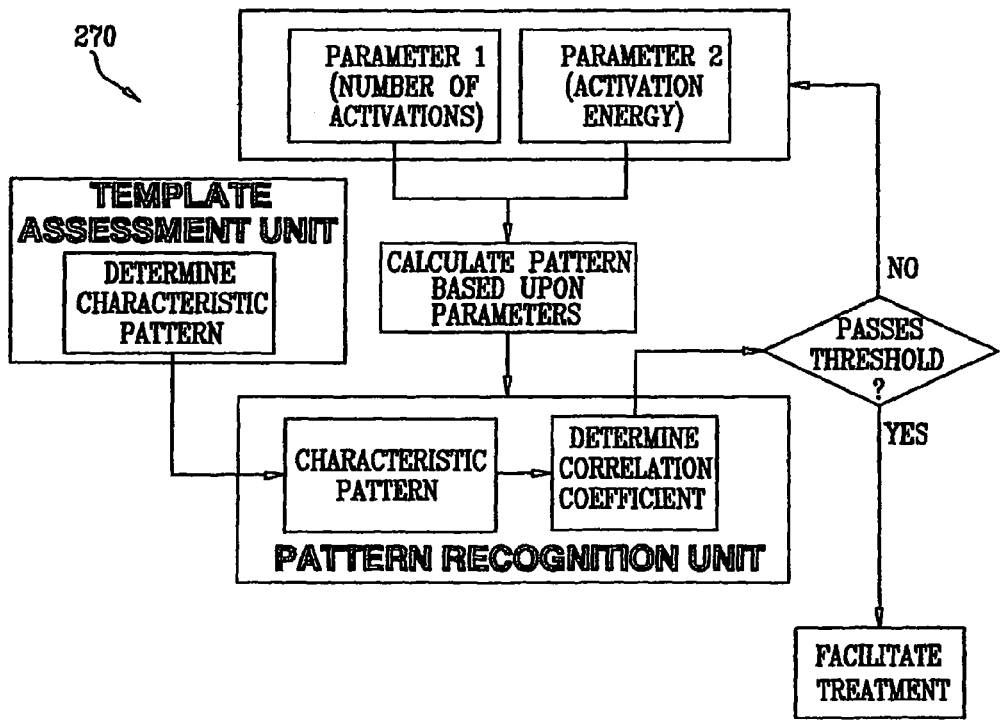
FIG. 25 is a flowchart of an algorithm used to determine if a subject is eating, in accordance with an embodiment of the present invention.

Reference is now made to FIG. 25, which is a flowchart of an algorithm 270 used to determine if a subject is eating, in accordance with an embodiment of the present invention. Control unit 20, described hereinabove, typically runs algorithm 270 to determine if the subject is eating, and facilitates a treatment of the subject, in response to determining that the subject is eating, in accordance with the techniques described herein. (Alternatively, control unit 20 does not facilitate a treatment of the subject in response to the determination.)

The control unit calculates a pattern based upon electrical activity detected in the subject's duodenum. In some embodiments, the calculated pattern may be a pattern that is based upon a single parameter of the detected electrical activity. For example, the calculated pattern may be the pattern of the activation energy curve, the slow-wave energy curve, the curve of the time frequency distribution of the duodenal electrical activity, a curve of the time variation of the number of activations per unit time of the duodenum, or a curve of the time variation of the number of activations per unit time of the slow-waves of the duodenum as defined hereinabove. Alternatively (as shown in algorithm 270), the control unit calculates a pattern based on a plurality of parameters of the detected electrical activity, for example, the pattern may be calculated by calculating the geometric mean of the number of activations per unit time and the activation energy curves of the detected electrical activity, or by calculating a mean or combination of two or more other variables.

The control unit comprises a pattern recognition unit which compares the calculated pattern to a characteristic pattern (for example, pattern 254 shown in FIG. 23). In some embodiments, the pattern recognition unit compares to the characteristic pattern, a calculated pattern that is based upon at least 2 minutes (typically 5-40 minutes, e.g. 15-30 minutes) of detected electrical activity. Typically, the output of the comparison of the calculated pattern to the characteristic pattern is a cross-correlation coefficient, and is determined using techniques known in the art. The magnitude of the cross-correlation coefficient typically depends only on the shapes of the calculated pattern and the characteristic pattern, and not on the magnitudes or the relative magnitudes of the patterns. In some embodiments, the pattern recognition unit does compare the magnitudes of the patterns. In response to the cross-correlation coefficient passing a threshold, the control unit facilitates a treatment of the subject, for example, administering a pharmaceutical (such as insulin) to the subject, driving a current into the subject's tissue, and/or one of the treatments described hereinabove. For some applications, the control unit only generates an indication of detected eating, and does not directly facilitate a treatment.

In some embodiments, the characteristic pattern is determined by a template assessment unit, which is typically a portion of the control unit. The template assessment unit analyzes parameters of the electrical activity of the subject's duodenum, when the subject is eating and when the subject is not eating. Based upon the analysis, the template assessment unit determines a subject-eating pattern that is characteristic of the subject when the subject is eating. The subject-eating pattern is used as the characteristic pattern by the pattern recognition unit. In some embodiments, the template assessment unit determines the subject eating pattern during a calibration period and, subsequent to the calibration period, the pattern recognition unit compares the calculated pattern to the subject-eating pattern, as determined during the calibration period. Alternatively, the template assessment unit updates the subject-eating pattern in an ongoing fashion over a long period of use of apparatus 21. In some embodiments, an eating pattern that is characteristic of a normal person eating, and that is not subject-specific, is used as the characteristic pattern.

In some embodiments, the control unit identifies an indication that the subject may be eating using, for example, one or more of the techniques described hereinabove (such as by running algorithm 120 or 130). In response to identifying the indication, the control unit initiates an interim treatment mode, facilitating a treatment of the subject, for example, by facilitating one or more of the treatments described hereinabove. Subsequently, the control unit may determine that the cross-correlation coefficient does not pass a threshold, indicating that the calculated pattern is not characteristic of an eating subject. In response to determining that the cross-correlation coefficient does not pass the threshold, the control unit stops the treatment. For example, in response to the cross-correlation coefficient not passing the threshold within 5-40 minutes (e.g., 20-30 minutes) of the initiation of the interim treatment mode, the control unit stops the treatment.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus, comprising:
   a sensing electrode configured to detect electrical activity of a duodenum of a subject; and
   a control unit configured, responsively to the detected electrical activity, to perform an action selected from the group consisting of: facilitating a treatment of the subject, and stopping a treatment of the subject,
   wherein the control unit is configured to calculate a pattern based on changes in the detected electrical activity over time, wherein the control unit comprises a pattern recognition unit configured to compare the calculated pattern to a predetermined characteristic pattern, and wherein the control unit is configured to perform the selected action responsively to the comparing.

2. The apparatus according to claim 1, wherein the pattern recognition unit is configured to compare the calculated pattern to the characteristic pattern irrespective of relative magnitudes of the calculated pattern and the characteristic pattern.

3. The apparatus according to claim 1, wherein the characteristic pattern includes a v-shaped pattern, and wherein the pattern recognition unit is configured to compare the calculated pattern to the v-shaped pattern.

4. The apparatus according to claim 1, wherein the control unit is configured to calculate the pattern based on changes in activation energy of the detected electrical activity over time.

5. The apparatus according to claim 1, wherein the control unit is configured to calculate the pattern based on changes in number of activations of the detected electrical activity per unit time.

6. The apparatus according to claim 1, wherein the control unit is configured to calculate the pattern based on changes over time of a parameter of the detected electrical activity selected from the group consisting of: slow-wave energy, time frequency distribution, and number of activations of slow-waves per unit time.

7. The apparatus according to claim 1, wherein the characteristic pattern includes an eating pattern that is characteristic of a person who is eating, and wherein the pattern recognition unit is configured to compare the calculated pattern to the eating pattern.

8. The apparatus according to claim 7, wherein the control unit comprises a template assessment unit configured to determine a subject-eating pattern that is characteristic of the subject when the subject is eating, and wherein the pattern recognition unit is configured to compare the calculated pattern to the subject-eating pattern.

9. The apparatus according to claim 1, wherein the pattern recognition unit is configured to compare the calculated pattern to the characteristic pattern by comparing a calculated pattern based on at least 2 minutes of the detected electrical activity to the characteristic pattern.

10. The apparatus according to claim 9, wherein the pattern recognition unit is configured to compare the calculated pattern to the characteristic pattern by comparing a calculated pattern based on up to 30 minutes of the detected electrical activity to the characteristic pattern.

11. The apparatus according to claim 1, wherein the pattern recognition unit is configured to compare the calculated pattern to the characteristic pattern by generating a cross-correlation coefficient indicative of a level of correlation between the calculated pattern and the characteristic pattern.

12. The apparatus according to claim 11, wherein the control unit is configured to perform the stopping of the treatment of the subject by:
   analyzing the detected electrical activity to identify an indication that the subject may be eating,
   in an interim treatment mode, facilitating the treatment in response to the analysis of the detected electrical activity, and
   stopping the treatment in response to the cross-correlation coefficient not passing a threshold.

13. The apparatus according to claim 11, wherein the control unit is configured to facilitate the treatment of the subject responsively to the comparing by facilitating the treatment in response to the cross-correlation coefficient passing a threshold.

14. A method, comprising:
   using a sensing electrode, detecting electrical activity of a duodenum of a subject; and
   in response to the detected electrical activity, performing an action selected from the group consisting of: treating the subject, and stopping a treatment of the subject,
   wherein performing the selected action in response to the detected electrical activity comprises:
      using a control unit, calculating a pattern based on changes in the detected electrical activity over time;
      using a pattern recognition unit, comparing the calculated pattern to a predetermined characteristic pattern; and
      performing the selected action in response to the comparing.

15. The method according to claim 14, wherein comparing the calculated pattern to the characteristic pattern comprises comparing the pattern to the characteristic pattern irrespective of relative magnitudes of the calculated pattern and the characteristic pattern.

16. The method according to claim 14, wherein comparing the calculated pattern to the characteristic pattern comprises comparing the calculated pattern to a v-shaped pattern.

17. The method according to claim 14, wherein calculating the pattern based on changes in the detected electrical activity over time comprises calculating the pattern based on changes in activation energy of the detected electrical activity over time.

18. The method according to claim 14, wherein calculating the pattern based on changes in the detected electrical activity over time comprises calculating the pattern based on changes in number of activations per unit time of the detected electrical activity over time.

19. The method according to claim 14, wherein calculating the pattern based on changes in the detected electrical activity over time comprises calculating the pattern based on changes over time of a parameter of the electrical activity selected from the group consisting of: slow-wave energy, time frequency distribution, and number of activations per unit time of slow-waves.

20. The method according to claim 14, wherein the characteristic pattern includes an eating pattern that is characteristic of a person who is eating, and wherein comparing the calculated pattern to the characteristic pattern comprises comparing the pattern to the eating pattern.

21. The method according to claim 20, further comprising determining a subject-eating pattern that is characteristic of the subject when the subject is eating, wherein comparing the calculated pattern to the characteristic pattern comprises comparing the pattern to the subject-eating pattern.

22. The method according to claim 14, wherein comparing the calculated pattern to the characteristic pattern comprises comparing a calculated pattern based on at least 2 minutes of the detected electrical activity to the characteristic pattern.

23. The method according to claim 22, wherein comparing the calculated pattern to the characteristic pattern comprises comparing a calculated pattern based on up to 30 minutes of the detected electrical activity to the characteristic pattern.

24. The method according to claim 14, wherein comparing the calculated pattern to the characteristic pattern comprises generating a cross-correlation coefficient indicative of a level of correlation between the calculated pattern and the characteristic pattern.

25. The method according to claim 24, wherein stopping the treatment comprises:
   analyzing the detected electrical activity to identify an indication that the subject may be eating,
   in an interim treatment mode, facilitating the treatment in response to the analysis of the detected electrical activity, and
   stopping the treatment in response to the cross-correlation coefficient not passing a threshold.

26. The method according to claim 24, wherein facilitating the treatment of the subject responsively to the comparing comprises facilitating the treatment in response to the cross-correlation coefficient passing a threshold.

* * * * *